(12) United States Patent
Scarantino et al.

(10) Patent No.: US 6,402,689 B1
(45) Date of Patent: Jun. 11, 2002

(54) METHODS, SYSTEMS, AND ASSOCIATED IMPLANTABLE DEVICES FOR DYNAMIC MONITORING OF PHYSIOLOGICAL AND BIOLOGICAL PROPERTIES OF TUMORS

(75) Inventors: Charles W. Scarantino, Raleigh; H. Troy Nagle, Durham; Leslie C. Hall, Raleigh; Jeffrey Mueller, Cary; Chang-Soo Kim, Raleigh, all of NC (US)

(73) Assignees: Sicel Technologies, Inc., Morrisville, NC (US); North Carolina State University, Raleigh, NC (US)

( * ) Notice: Subject to any disclaimer, the term of this patent is extended or adjusted under 35 U.S.C. 154(b) by 0 days.

(21) Appl. No.: 09/407,359

(22) Filed: Sep. 29, 1999

Related U.S. Application Data

(60) Provisional application No. 60/102,447, filed on Sep. 30, 1998.

(51) Int. Cl.[7] .............................. A61B 5/00; A61K 49/00
(52) U.S. Cl. ...................... 600/300; 128/903; 128/904; 128/920; 600/301; 600/361; 600/407; 600/326; 424/9.1; 424/422
(58) Field of Search ................................ 600/300–301, 600/326–327, 309, 361–365, 407, 436, 476, 1–7; 128/903, 904, 920–925; 424/9.1, 422, 423

(56) References Cited

U.S. PATENT DOCUMENTS

| | | |
|---|---|---|
| 3,638,640 A | 2/1972 | Shaw |
| 3,972,320 A | 8/1976 | Kalman |
| 4,163,380 A | 8/1979 | Masoner |
| 4,326,535 A | 4/1982 | Steffel et al. |
| 4,361,153 A | 11/1982 | Slocum et al. |

(List continued on next page.)

FOREIGN PATENT DOCUMENTS

| | | |
|---|---|---|
| DE | 3219558 A1 | 12/1983 |
| DE | 4341903 A1 | 6/1995 |
| EP | 0420177 A1 | 3/1991 |
| EP | 0 420 177 A1 | 4/1991 |

(List continued on next page.)

OTHER PUBLICATIONS

Cosofret et al., "Microfabricated sensor arrays sensitive to pH and K+ for ionic distribution measurements in the beating heart," *Analytical Chemistry*, vol. 67, pp. 1647–1653 (1995).

(List continued on next page.)

*Primary Examiner*—Kevin Shaver
*Assistant Examiner*—Michael C Astorino
(74) *Attorney, Agent, or Firm*—Myers Bigel Sibley & Sajovec, P.A.

(57) ABSTRACT

Methods of monitoring and evaluating the status of a tumor undergoing treatment includes monitoring in vivo at least one physiological parameter associated with a tumor in a subject undergoing treatment, transmitting data from an in situ located sensor to a receiver external of the subject, analyzing the transmitted data, repeating the monitoring and transmitting steps at sequential points in time and evaluating a treatment strategy. The method provides dynamic tracking of the monitored parameters over time. The method can also include identifying in a substantially real time manner when conditions are favorable for treatment and when conditions are unfavorable for treatment and can verify or quantify how much of a known drug dose or radiation dose was actually received at the tumor. The method can include remote transmission from a non-clinical site to allow oversight of the tumor's condition even during non-active treatment periods (in between active treatments). The disclosure also includes monitoring systems with in situ in vivo biocompatible sensors and telemetry based operations and related computer program products.

72 Claims, 16 Drawing Sheets

U.S. PATENT DOCUMENTS

| | | | |
|---|---|---|---|
| 4,397,313 A | 8/1983 | Vaguine | |
| 4,397,314 A | 8/1983 | Vaguine | |
| 4,416,283 A | 11/1983 | Slocum | |
| 4,431,004 A | 2/1984 | Bessman et al. | |
| 4,494,545 A | 1/1985 | Slocum et al. | |
| 4,519,401 A | 5/1985 | Ko et al. | |
| 4,523,279 A | 6/1985 | Sperinde et al. | |
| 4,541,901 A | 9/1985 | Parker et al. | |
| 4,543,953 A | 10/1985 | Slocum et al. | |
| 4,556,063 A | 12/1985 | Thompson et al. | |
| 4,571,292 A | 2/1986 | Liu et al. | 204/412 |
| 4,571,589 A | 2/1986 | Slocum et al. | |
| 4,575,676 A | 3/1986 | Palkuti | |
| 4,625,733 A | 12/1986 | Säynäjäkangas | |
| 4,638,436 A | 1/1987 | Badger et al. | |
| RE32,361 E | 2/1987 | Duggan | |
| 4,651,741 A | 3/1987 | Passafaro | |
| 4,655,880 A | 4/1987 | Liu | 204/1 T |
| 4,681,111 A | 7/1987 | Silvian | |
| 4,703,756 A | 11/1987 | Gough et al. | |
| 4,719,919 A | 1/1988 | Marchosky et al. | |
| 4,750,495 A | 6/1988 | Moore et al. | |
| 4,769,547 A | 9/1988 | Uber, III | |
| 4,793,825 A | 12/1988 | Benjamin et al. | |
| 4,796,641 A | 1/1989 | Mills et al. | |
| 4,804,847 A | 2/1989 | Uber, III | |
| 4,846,191 A | 7/1989 | Brockway et al. | |
| 4,847,617 A | 7/1989 | Silvian | |
| 4,900,422 A | 2/1990 | Bryan et al. | |
| 4,919,141 A | 4/1990 | Zier et al. | |
| 4,935,345 A | 6/1990 | Guilbeau et al. | |
| 4,944,299 A | 7/1990 | Silvian | |
| 4,958,645 A | 9/1990 | Cadell et al. | |
| 4,961,422 A | 10/1990 | Marchosky et al. | |
| 4,970,391 A | 11/1990 | Uber | |
| 4,976,266 A | 12/1990 | Huffman et al. | |
| 4,989,601 A | 2/1991 | Marchosky et al. | |
| 5,008,546 A | 4/1991 | Mazziotta et al. | 250/366 |
| 5,012,411 A | 4/1991 | Policastro et al. | |
| 5,098,547 A | 3/1992 | Bryan et al. | |
| 5,109,850 A | 5/1992 | Blanco et al. | |
| 5,117,824 A | 6/1992 | Keimel et al. | |
| 5,126,937 A | 6/1992 | Yamaguchi et al. | |
| 5,127,404 A | 7/1992 | Wyborny et al. | |
| 5,137,022 A | 8/1992 | Henry | |
| 5,163,380 A | 11/1992 | Duffy et al. | |
| 5,186,172 A | 2/1993 | Fiddian-Green | |
| 5,193,538 A | 3/1993 | Ekwall | |
| 5,197,466 A | 3/1993 | Marchosky et al. | |
| 5,205,294 A | 4/1993 | Flach et al. | |
| 5,215,887 A | 6/1993 | Saito | |
| 5,264,843 A | 11/1993 | Silvian | |
| 5,309,085 A | 5/1994 | Sohn | 324/71.5 |
| 5,314,450 A | 5/1994 | Thompson | |
| 5,324,315 A | 6/1994 | Grevious | |
| 5,330,634 A | 7/1994 | Wong et al. | |
| 5,354,314 A | 10/1994 | Hardy et al. | |
| 5,354,319 A | 10/1994 | Wyborny et al. | |
| 5,355,880 A | 10/1994 | Thomas et al. | |
| 5,372,133 A | 12/1994 | Hogen et al. | |
| 5,383,909 A | 1/1995 | Keimel | |
| 5,425,361 A | 6/1995 | Fenzlein et al. | |
| 5,431,171 A | 7/1995 | Harrison et al. | |
| 5,444,254 A | 8/1995 | Thomson | |
| 5,466,246 A | 11/1995 | Silvian | |
| 5,470,345 A | 11/1995 | Hassler et al. | |
| 5,476,488 A | 12/1995 | Morgan et al. | |
| 5,480,415 A | 1/1996 | Cox et al. | |
| 5,481,262 A | 1/1996 | Urbas et al. | |
| 5,497,772 A | 3/1996 | Schulman et al. | |
| 5,505,828 A | 4/1996 | Wong et al. | |
| 5,507,786 A | 4/1996 | Morgan et al. | |
| 5,517,313 A | 5/1996 | Colvin, Jr. | |
| 5,535,752 A | 7/1996 | Halperin et al. | |
| 5,538,005 A | 7/1996 | Harrison et al. | |
| 5,545,187 A | 8/1996 | Bergstrom et al. | |
| 5,549,113 A | 8/1996 | Halleck et al. | |
| 5,549,654 A | 8/1996 | Powell | |
| 5,556,421 A | 9/1996 | Prutchi et al. | |
| 5,562,713 A | 10/1996 | Silvian | |
| 5,564,434 A | 10/1996 | Halperin et al. | |
| 5,571,148 A | 11/1996 | Loeb et al. | |
| 5,591,217 A | 1/1997 | Barreras | |
| 5,593,430 A | 1/1997 | Renger | |
| 5,620,472 A | 4/1997 | Rahbari | |
| 5,620,475 A | 4/1997 | Magnusson | |
| 5,620,479 A | 4/1997 | Diederich | |
| 5,626,630 A | 5/1997 | Markowitz et al. | |
| 5,626,862 A | 5/1997 | Brem et al. | |
| 5,628,324 A | 5/1997 | Sarbach | |
| 5,630,413 A | 5/1997 | Thomas et al. | |
| 5,720,771 A | 2/1998 | Snell | |
| 5,732,704 A | 3/1998 | Thurston et al. | 128/659 |
| 5,744,804 A | 4/1998 | Meijer et al. | 250/369 |
| 5,744,805 A | 4/1998 | Raylman et al. | 250/370.01 |
| 5,759,199 A | 6/1998 | Snell et al. | |
| 5,791,344 A | 8/1998 | Schulman et al. | |
| 5,814,089 A | 9/1998 | Stokes et al. | |
| 5,833,603 A | 11/1998 | Kovacs et al. | |
| 5,879,375 A | 3/1999 | Larson et al. | |
| 5,891,179 A | 4/1999 | Er et al. | |
| 5,918,110 A | 6/1999 | Abraham-Fuchs et al. | |
| 5,932,879 A | 8/1999 | Raylman et al. | 250/370.06 |
| 6,047,214 A | 4/2000 | Mueller et al. | 607/61 |
| 6,076,009 A | 6/2000 | Raylman et al. | 600/436 |
| 6,240,312 B1 * | 5/2001 | Alfano et al. | 600/476 |

FOREIGN PATENT DOCUMENTS

| | | |
|---|---|---|
| EP | 0245073 B1 | 2/1993 |
| EP | 0537761 A2 | 4/1993 |
| EP | 0386218 B1 | 10/1996 |
| WO | WO 97/33513 | 9/1997 |
| WO | WO 98/02209 A3 | 1/1998 |
| WO | WO 98/02209 A2 | 1/1998 |
| WO | WO 98/43701 | 10/1998 |
| WO | PCT/US 98/05965 | 12/1998 |
| WO | WO 98/58250 | 12/1998 |
| WO | WO 00/29096 | 5/2000 |

OTHER PUBLICATIONS

Marzouk et al., "Electrodeposited Iridium Oxide pH Electrode for Measurement of Extracellular Myocardial Acidosis during Acute Ischemia," Anal. Chem., vol. 70, pp. 5054–5061 (1998).

Wolf et al., "Potential of microsensor–based feedback bioactuators for biophysical cancer treatment," Biosensors & Bioelectronics, vol. 12, pp. 301–309 (1997).

PCT International Search Report, International Application No. PCT/US99/22638, mailed Jan. 27, 2000.

International Search Report, PCT/US00/08310; Oct. 25, 2000.

Y. Oshima et al; Development of Micro–Telemetering Multi–Sensor Capsule System with newly developed LSI for the clinical applications; Transducers '87, The $4^{th}$ International Conference on Solid–State Sensors and Actuators; pp 163–166.

Hines; Advanced Biotelemetry Systems for Space Life Sciences: PH Telemetry, Biotelementry XIII, Mar. 26–31, 1995 pp 131–137.

Barber et al., "Comparison of NaI(Tl), CdTe, and $HgI_2$ surgical probes: Physical characterization, " Med. Phys. 18 (3), pp. 373–381 (May/Jun. 1991).

Berthold et al., "Method for in–situ detection of tritium in water," McDermott Technology Inc./RDTPA 99–03, pp. 1–9 (Sep. 19–22, 1999).

Dimitrakopoulou et al., "Studies with positron emission tomography after systemic administration of fluorine–18–uracil in patients with liver metastases from colorectal carcinoma," J. Nuc. Med., 34 (7), pp. 1075–1081 (Jul. 1993).

Dewhirst et al., "Soft–tissue sarcomas: MR imaging and MR spectroscopy for prognosis and therapy monitoring," Radiology, pp. 847–853 (Mar. 1990).

Hamburger et al., "Primary bioassay of human tumor stem cells," Science, vol. 197, pp. 461–463 (Jul. 29, 1977).

Hoffman et al., "Intraoperative probes and imaging probes," Eur. J. Nuc. Med., vol. 26, No. 8 pp. 913–935 (Aug. 1999).

Kastrissios et al., "Screening for sources of interindividual pharmacokinetic variability in anticancer drug therapy: utility of population analysis," Cancer Investigation 19(1), pp. 57–64 (2001).

Kern, David, "Tumor chemosensitivity and chemoresistance assays," Am. Cancer Soc., vol. 79, No. 7, pp. 1447–1450 (Apr. 1, 1997).

Kissel et al., "Noninvasive determination of the arterial input function of an anticancer drug from dynamic PET scans using the population approach," Med. Phys. 26 (4), pp. 609–615 (Apr. 1999).

Koutcher et al., "Potentiation of a three drug chemotherapy regimem by radiation," Cancer Research 53, pp. 3518–3523 (Aug. 1, 1993).

Piwnica–Worms et al., "Functional imaging of multi–drug–resistant P–glycoprotein with an organotechnetium complex," Cancer Research 53, pp. 977–984 (Mar. 1, 1993).

Presant et al., "Human tumor fluorouracil trapping: clinical corrections of in vivo $^{19}F$ nuclear magnetic resonance spectroscopy pharmacokinetics," J. Clinical Oncology, 8 (11) pp. 1868–1873 (Nov. 1990).

Presant et al., "Enhancement of fluorouracil uptake in human colorectal and gastric cancers by interferon or by high–dose methotrexate: an in vivo human study using noninvasive $^{19}F$ –magnetic resonance spectroscopy," J. Clinical Oncology, 18 (2) pp. 255–261 (Jan. 2000).

Stevens et al., "5–Flourouracil metabolism monitored in vivo by $^{19}F$ NMR," Br. J. Cancer 50, pp. 113–117 (1984).

Von Hoff et al., "Selection of cancer chemotherapy for a patient by an in vivo assay versus a clinician," J. Nat'l. Cancer Inst. 82 (2), pp. 110–116 (Jan. 17, 1990).

Wolf et al., "Tumor trapping of 5–fluorouracil: in vivo $_{19}F$ NMR spectroscopic pharmacokinetics in tumor–bearing humans and rabbits," Proc. Natl. Acad. Sci. USA, 87, pp. 492–496 (Jan. 1990).

Yarnell et al., "Drug assays on organ cultures of biopsies from human tumours," Brit. Med., J., 2, pp. 490–491 (1964).

Zanzonico et al., "The intraoperative gamma probe: basic principles and choices available," Seminars in Nucl. Med., XXX(1), pp. 33–48 (Jan. 2000).

Ludwig Institute for Cancer Research, Annual Report 1995, http://www.icp.ucl.ac.be/report95/licr95.html.

Brochure, "Be as Smart as you can be with BMDS and SmartAlec™ your partners in intelligence," Bio Medic Data Systems, Inc. (©1999).

Brochure, "Come along for the incredible journey in the development of the IPTT–200," Bio Medic Data Systems, Inc. (©2000).

Griffiths et al., "The OxyLite: a fibre–optic oxygen sensor," British J. of Radiology, vol. 72 pp. 627–630 (1999).

Mackay, "Bio–Medical Telemetry, Sensing and Transmitting Biological Information from Animals and Man" Second edition. New York, NY: IEEE Press (1993).

Mittal et al., Evaluation of an Ingestible Telemetric Temperature Sensor for Deep Hyperthermia Applications,: Int. J. Radiation Oncology Biol. Phys., vol. 21, pp. 1353–1361 (1991).

Taylor et al., "The Forces in the Distal Femur and the Knee During Walking and Other Activities Measured by Telemetry," J. of Anthroplasty, vol. 13, No. 4, pp. 428–437 (1998).

Watanabe et al., "A Preliminary Report on Continuous Recording of Salivary pH Using Telemetry in an Edentulous Patient," Int'l J. Proshodontics, vol. 12, No. 4, pp. 313–317 (1999).

Webster, Editor, "Design of Cardiac Pacemakers," IEEE Press, pp. 155–157.

Zuckier et al., "Remotely Pollable Geiger–Muller Detector for Continuous Monitoring of Iodine–131 Therapy Patients," J. of Nuclear Med., vol. 39, No. 9, pp. 1558–1562 (9/98).

Small Business Innovation Research Program Phase One Grant Application entitled "An Implantable Multi–channel System for Monitoring Tumors," submitted on or about Dec. 1996 to U.S. Public Health Service.

Small Business Innovation Research Program Phase One Grant Application entitled "An Implantable Multi–channel System for Monitoring Tumors," resubmitted with revisions on or about Aug. 1997 to the National Institute of Health.

Small Business Innovation Research Program Phase One Grant Application entitled "An Implantable Multi–channel System for monitoring Tumors," resubmitted to the U.S. funding authority on or about Apr. 1998.

* cited by examiner

REAL-TIME MONITORING

REMOTE-ONGOING DYNAMIC MONITORING

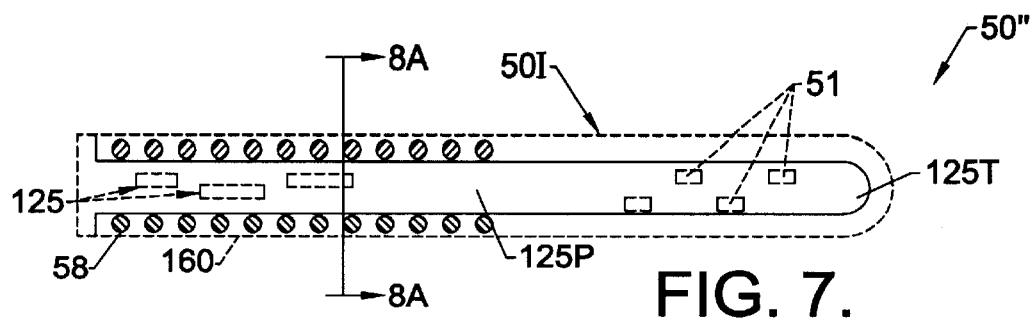
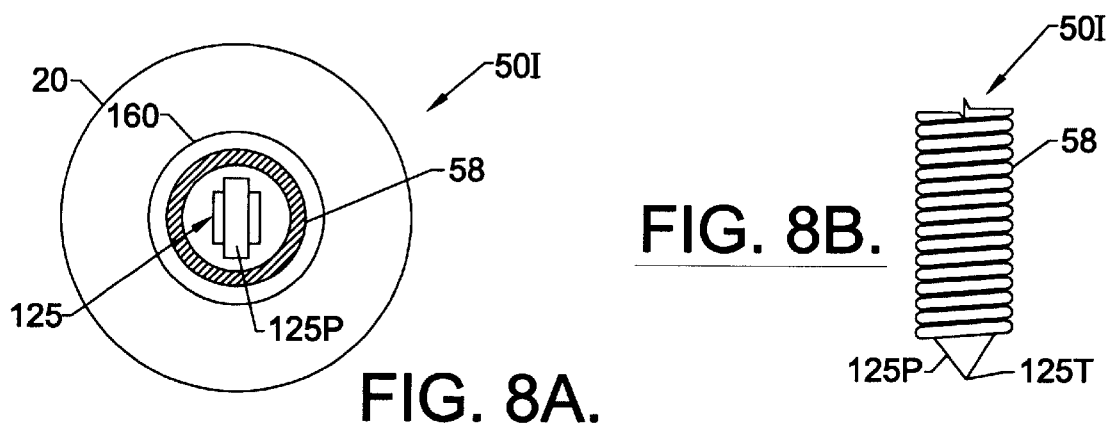
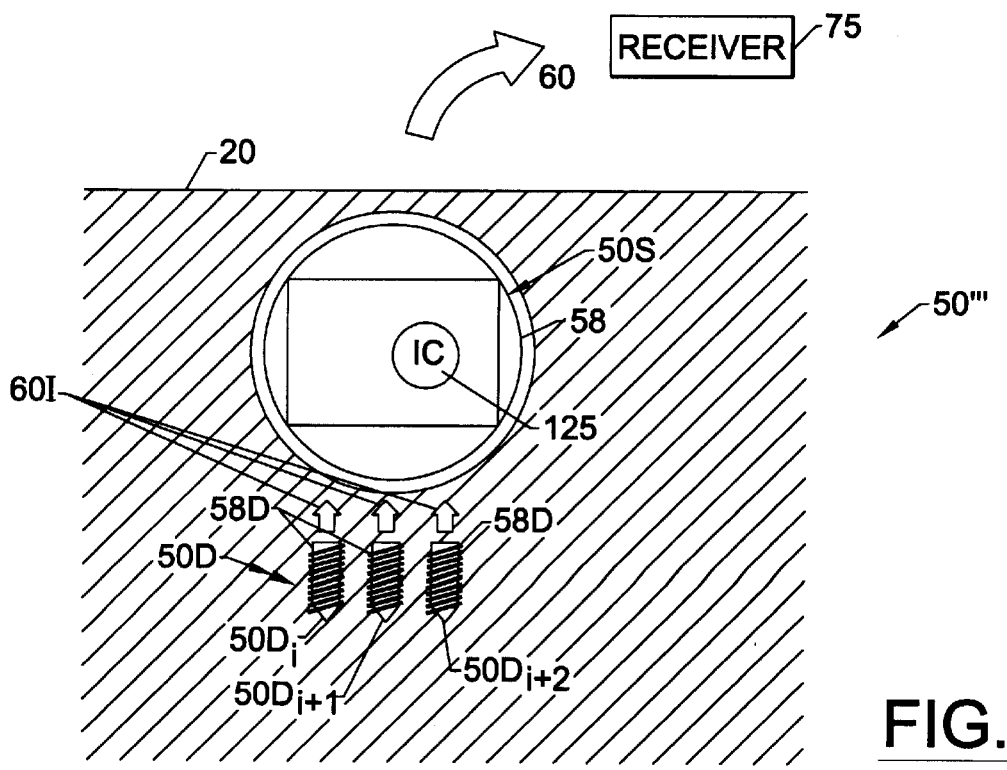

IC BLOCK DIAGRAM

IC LAYOUT

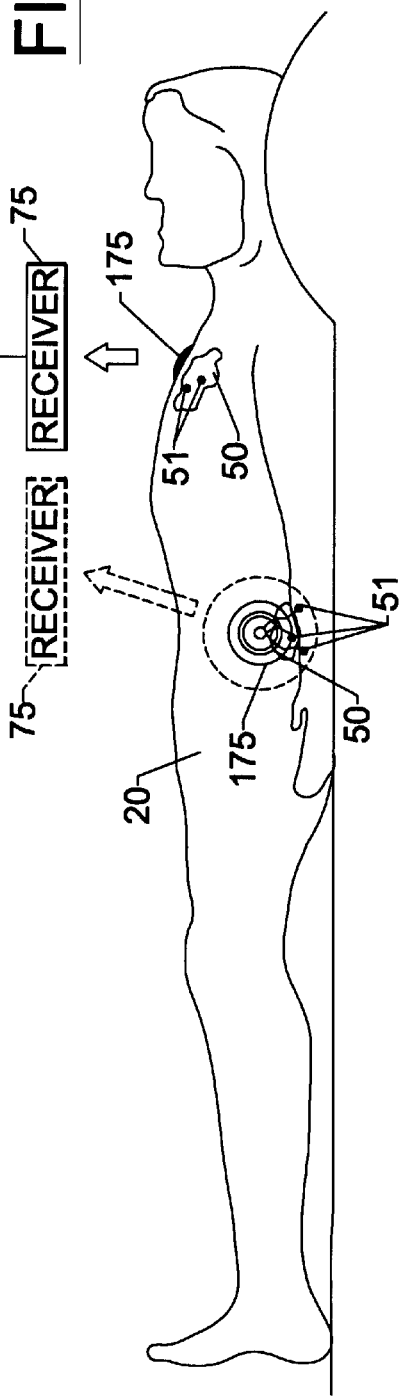
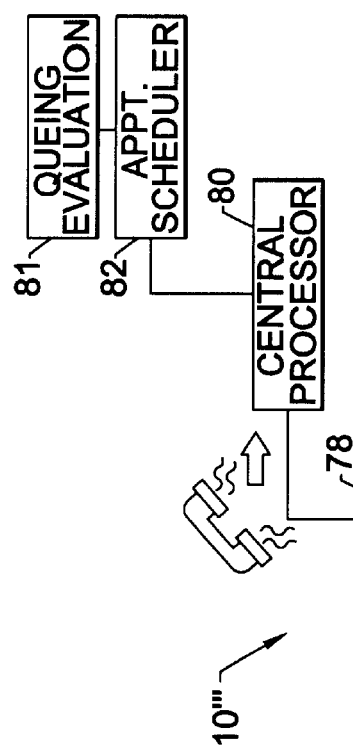
FIG. 19A.
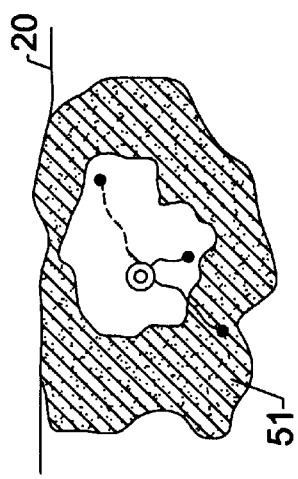
FIG. 19B.

Operating principle of self-calibrating, *IN SITU, IN VIVO* microsensor. The microenvironment controlled by the magnitude and direction of the generating current; oxygen-saturation or oxygen-depletion depends on anodic or cathodic behavior of GE.

SURFACE CLEANING
METAL (Pt) DEPOSITION
PHOTOLITHOGRAPHY
METAL ETCHING

POLYIMIDE COATING
POLYIMIDE LITHOGRAPHY
POLYIMIDE COATING (2nd)
POLYIMIDE LITHOGRAPHY

ELECTROPLATING (InO$_2$, Au, AgCl/Ag)
PERMEABLE MEMBRANE CASTING

METHODS, SYSTEMS, AND ASSOCIATED IMPLANTABLE DEVICES FOR DYNAMIC MONITORING OF PHYSIOLOGICAL AND BIOLOGICAL PROPERTIES OF TUMORS

RELATED APPLICATIONS

This application claims priority from Provisional Application No. 60/102,447 filed on Sep. 30, 1998. The contents of this application are hereby incorporated by reference herein.

FIELD OF THE INVENTION

This invention relates to diagnostic medical instruments and procedures, and more particularly to implantable devices and methods for monitoring physiological parameters.

BACKGROUND OF THE INVENTION

The availability of a system and device capable of monitoring changes within any cell population of interest would be an important addition to the cancer treatment armamentarium and one that will fill a need by making available more precise knowledge of the most sensitive time(s) for treating a tumor cell population. This vital information could aid in the delivery of highly specific individual treatment regime rather than the empirical and somewhat generalized treatment plans of today.

The in vitro study of malignant cell populations have established important general principles by which clinical treatment protocols are developed. These principles have established differences between malignant and normal cell populations and have been employed in the treatment of malignant disease. There have been many attempts to exploit these differences, both in pre-clinical and clinical studies, in order to attempt to obtain total tumor cell kill and improved cure rates. One of the major obstacles in achieving this goal has been the difficulty in minimizing normal tissue toxicity while increasing tumor cell kill (therapeutic index). Thus, presently, most treatment strategies employ an empirical approach in the treatment of malignant disease. That is, the timing of delivery and dose of cytotoxic agents are guided more by the response and toxicity to normal tissue than by the effects on the malignant cell population. A major deficiency of this empirical approach is the lack of an efficient method or technique to provide accurate information on the dynamic changes during treatment (which can be extended over a long period of time) that occur within a malignant cell population. Making this invaluable information available to attending physicians can allow clinicians to exploit the revealed differences between malignant and normal cells, and hence improve the treatment procedures, to achieve better outcomes.

Much of the research in tumor biology has been involved in exploring the cellular, biochemical, and molecular difference between tumor and normal cells in order to improve the therapeutic index. Early cell kinetic studies revealed that cancer cells do not divide faster than normal cells, but rather a larger proportion of the cell population is dividing (Young et al., 1970). At that time, the failure to cure more tumors was attributed to a variation in growth characteristics. In the 1980's, it was proposed that these failures were due to development of resistance of tumor cells through mutations of an unstable genome (Goldie et al., 1984). Later studies suggested that the mechanism for tumor cell survival rests on expression of a gene that codes for a specific protein that expels or extrudes the cytotoxic agents from the cell (Chaudhary et al., 1992). More recently, it has been suggested that resistance is related to dysregulation of the cell cycle which alters the rates of cell growth (Lowe et al., 1994). Additional factors associated with failure to eliminate or effect improved cure rate include hypoxic cell populations, cell proliferation variants, cell differentiation agents, and cell cycle sensitive stages. The ability to monitor these changes during and following any treatment could offer a more precise knowledge of the most sensitive portions of any cell population and aid in the delivery of a more individualized and less empirical or generalized treatment program.

There have been a number of attempts to study certain of the dynamic changes occurring within a cell population, but these attempts generally lack the ability to monitor the changes on a real time basis. Indeed, these methods typically provide information at one point in time and most are designed to provide information on one particular function or parameter. In addition, most of the conventional methods can be expensive as well as time consuming. This can be problematic for patients undergoing extended treatment periods typical of radiation and or drug or chemotherapy, especially when it is desirable to follow dynamic changes both during an active treatment and subsequent to the active treatment throughout a treatment period.

The most reliable current monitoring technique is the biopsy. A biopsy can be taken at any time and can provide significant amount of information. However, it is impractical to biopsy each day and, even if one could, the time delay created in performing the various tests on the sample means that the information received by the physician is not an accurate representation of the patient's current condition. In addition to biopsy material, the radiological techniques of NMR and PET scanning can obtain, respectively, specific biological (cell cycle phase) and physiological (phosphorus) information, but both are sufficiently expensive that repetitive or daily information is rarely available. The radioactive labeling of specific antibodies or ligands is another available technique, but this method has many of the same problems noted above with the other assays.

In addition, over time, tumors progress through periods wherein they are less robust and, thus, potentially more susceptible to treatment by radiation or drug therapy. Providing a monitoring system which can continuously or semi-continuously monitor and potentially identify such a susceptible condition could provide welcome increases in tumor destruction rates. Further, especially for regionally targeted tumor treatment therapies, it can be difficult to ascertain whether the desired dose was received at the tumor site, and if so received, it can be difficult to assess its efficacy in a relatively non-invasive manner. Thus, there is a need for a monitoring system which can quantify and/or assess the localized or regional presence of a target drug.

Although much of the particular tumor-specific and/or internal systemic information which may definitively identify the most vulnerable tumor stage and, thus, the preferred active treatment period, is still relatively unsettled (as is the ultimate definitive cure or treatment protocol), various researchers have proposed several potentially important physiological and/or biological parameters such as oxygenation, pH, and cell proliferation which may relate to tumor vulnerability or susceptibility, and thus impact certain treatment strategies.

For example, in the article "Oxygen tension measurements of tumors growing in mice," it is proposed that it may be helpful to assess hypoxia in tumors during treatment. Adam et al., Int. J. Radiation Oncology Biol. Phys., Vol. 45, 1998, pp. 171–180. In addition, tumor hypoxia has been proposed to have an impact on the effectiveness of radiation therapy. See Seminars in Radiation Oncology, Vol. 8, 1998, pp. 141–142. Similarly, the authors of "Development of targeting hyperthermia on prostatic carcinoma and the role of hyperthermia in clinical treatment" note that there is a need for a way to assess temperature at the site of the tumor during therapy. Ueda et al., Jpn. J. Hyperthermic Oncol., Vol. 15 (supplement), 1999, pp. 18–19. Moreover, Robinson et al. opines that it is important to know the tumor oxygenation level and blood flow. See Robinson et al., "MRI techniques for monitoring changes in tumor oxygenation in blood flow," Seminars in Radiation Oncology, Vol. 8, 1998, pp. 197–207. Unfortunately, tumor oxygenation can vary and there is evidence to suggest that tumor oxygenation is in a continuous state of flux. See Dewhirst, "Concepts of oxygen transport at the microcirculatory level, " Seminars in Radiation Oncology, Vol. 8, 1998, pp. 143–150. This flux makes a dynamic monitoring method important for identifying when the tumor oxygenation level is such that a more active treatment strategy may be desired. In addition, tumor pH has been suggested as an exploitable parameter for drug design for tumor treatments. See Leo E. Gerweck, "Tumor pH: Implications for Treatment and Novel Drug Design", 8 Seminars in Radiation Oncology No. 5, pp. 176–182 (July 1998).

In the past, various biotelemetry devices and implantable sensors have been proposed to monitor cardiac conditions or physiological parameters associated with glucose or temperature. For example, U.S. Pat. No. 5,791,344 to Schulman et al. entitled "Patient Monitoring System," proposes a system to monitor the concentration of a substance in a subject's blood wherein one enzymatic sensor is inserted into a patient to monitor glucose and then deliver insulin in response thereto. Similarly, PCT US98 05965 to Schulman et al, entitled "System of Implantable Devices for Monitoring or Affecting Body Parameters," proposes using microsensors and/or microstimulators to sense glucose level, $O_2$ content, temperature, etc. There are also a number of implantable medical devices and systems which monitor physiological data associated with the heart via telemetry. One example of this type of device is described in U.S. Pat. No. 5,720,771 to Snell entitled, "Method and Apparatus for Monitoring Physiological Data From an Implantable Medical Device." The contents of these applications are hereby incorporated by reference as if recited in full herein.

In addition, unlike conventional implanted sensors, tumor monitoring systems and/or sensors used to monitor tumors can be exposed to a relatively harsh environment during a treatment protocol or strategy which can extend over a period of weeks, or even months (such as applied heat, chemicals and/or radiation). Further, such a harsh environment, coupled with an extended treatment period, can affect the function of the device and thus, potentially corrupt the measurement data it generates.

In view of the foregoing, there remains a need for tumor monitoring systems and devices which can, inter alia, monitor the physiological and/or biological condition of a tumor during a treatment cycle to identify enhanced or favorable treatment windows to potentially increase in vivo treatment efficacy associated with such treatment.

OBJECTS AND SUMMARY OF THE INVENTION

It is therefore an object of the present invention to provide monitoring systems, methods, and associated devices which can dynamically monitor multiple tumor physiological and biological parameters and/or changes associated with tumors to identify enhanced or favorable treatment conditions to thereby establish a patient-specific treatment delivery time.

It is also an object of the present invention to provide a dynamic and/or semi-continuous (or even substantially continuous) tumor monitoring system which can be remotely monitored on an ongoing basis during treatment.

It is an additional object of the present invention to provide an implantable cancerous tumor sensor system which is cost-effective and which can provide sufficient ongoing, and preferably substantially real-time, information pertaining to the physiological and/or biological condition of the tumor during a treatment period in a way which provides the information to the physician to assist in therapeutic decisions.

It is yet another object of the present invention to provide a tumor monitoring system which can provide real-time information regarding cancerous tumor physiology as an adjunct to therapy.

It is an additional object of the present invention to provide a cancerous tumor monitoring system which can provide clinically effective regionally specific data representative of the dynamic effects of cytotoxic agents on cell populations during an extended treatment period.

It is another object of the present invention to provide an implantable oxygen sensor configuration which is particularly suitable for monitoring the oxygenation and/or pH level in a tumor.

It is yet another object of the present invention to provide system related sensors and computer program products for identifying when a tumor exhibits potential vulnerability or susceptibility based on data associated with an in vivo in situ sensor which provides measurements of parameters associated with a tumor.

It is another object of the present invention to provide a method of remotely monitoring parameters associated with a patient's cancerous tumor physiology and alerting a clinician of the presence of a condition indicating a favorable treatment period or the need for other evaluation or adjustment in an ongoing planned treatment strategy.

It is an additional object of the present invention to provide a system for monitoring tumors which can indicate (in substantially real time) whether conditions are favorable or unfavorable for an active treatment such as drug delivery, hyperthermia, chemotherapy, or radiation therapy.

It is still another object of the present invention to provide a system or computer program product for analyzing a plurality of measurements generated by at least one implanted sensor and analyzing the measurements and identifying the presence or absence of one or more predetermined conditions associated with the measurements to alert the clinician of the existence of a potentially vulnerable and desired treatment phase for a tumor.

These and other objects of the present invention are provided by a bio-telemetry based tumor monitoring system with in vivo, in situ sensors positioned to monitor multiple selected parameters representative of the status of a tumor or tumors in a subject.

More particularly, a first aspect of the present invention is a method of monitoring and evaluating the status of a tumor undergoing treatment. The method includes the steps of monitoring in vivo at least one physiological parameter associated with a tumor in a subject undergoing treatment with an in situ sensor. Data associated with at least one monitored physiological parameter is transmitted from an in situ positioned sensor to a receiver external of the subject. The transmitted data is analyzed to determine how the tumor is responding to treatment. Additional data is transmitted and analyzed periodically at a plurality of sequential points in time, and a tumor treatment strategy is evaluated based on the analyzing step.

In a preferred embodiment, the transmitting and analyzing steps are repeated sufficiently often (such as at least every 24 hours, and more preferably at least hourly, at least during particular time segments of treatment) to track variation in at least one monitored parameter and thereby assess the behavior of the tumor over time. It is also preferred that at least one parameter is a plurality of parameters, and that the analyzing step defines a plurality of test conditions associated with the monitored parameters to evaluate the treatment corresponding to the condition of the tumor (such as the efficacy of treatment or the presence or absence of favorable indices of treatment). If the transmitted data satisfies at least one test condition related to the monitored physiological parameters, a clinician can then be alerted as to the presence of at least one of a favorable and unfavorable treatment window for delivering a subsequent active treatment to the tumor. Preferably, the favorable treatment window corresponds to the identification of a tumor susceptibility or vulnerability phase.

It is also preferred that the transmitting step comprises transmitting data from the home site of the patient to a remote clinical site thereby allowing real-time remote dynamic monitoring of the physiological parameter. Further, it is also preferred that the transmitting step is repeated temporally proximate to a subsequent active treatment delivery time to provide real-time information regarding the desirability of the timing of a planned treatment or the efficacy of a delivered treatment.

Another aspect of the present invention is directed to a tumor monitoring system for evaluating the efficacy of radiation or drug treatment and/or identifying enhanced or favorable active treatment windows. The system comprises at least one sensor unit comprising a plurality of sensor elements and associated sensor electronics configured for in vivo, in situ contact with a cancerous tumor in a subject undergoing treatment. The sensor elements are configured to sense a plurality of different physiological parameters associated with the tumor and wirelessly transmit the sensed data. The sensor units have an implanted service life of at least about 6–10 weeks, and more preferably at least about 8–12 weeks. The system also includes a remote receiver in wireless communication with the at least one sensor unit, and is configured to receive the transmitted sensor data. The receiver is positioned external to the subject.

The system also preferably includes a data processor configured to receive the transmitted data including computer program code means for reviewing and adjusting the received data to correct for variations attributed to environmental exposure in the subject.

An additional aspect of the present invention is directed to a computer program product for monitoring and analyzing the condition of a tumor undergoing treatment. The computer program product comprises a computer readable storage medium having computer readable program code means embodied in the medium. The computer-readable program code means comprises computer readable program code means for commencing a first wireless data transmission from an in situ sensor with at least one sensor element, where the at least one sensor element is positioned in a subject proximate to a tumor undergoing treatment to monitor at least one physiological or biological parameter of the tumor, and the data transmission includes data corresponding to the output of the at least one sensor element. The product also includes computer readable program code means for commencing a second wireless data transmission from the in situ sensor temporally separate from the first wireless data transmission and computer readable program code means for tracking variation between the first and second data transmissions to provide a dynamic behavioral model of the tumor's response to the treatment.

Preferably, the computer program product further comprises computer readable program code means to evaluate the efficacy of the treatment corresponding to either of a predetermined absolute value or relative change of the monitored at least one physiological parameter over time. It is also preferred that the computer program product further comprises computer readable program code means for commencing ongoing periodic data transmissions over a predetermined (and/or adaptively determined or scheduled) time period, and computer readable program code means for analyzing the data transmissions to identify potential enhanced or favorable active treatment opportunities.

Advantageously, and in contrast to the empirical treatment strategies employed in the past to schedule active treatments (such as chemotherapy or radiation therapy), the present invention now allows targeted tumor treatment directed by the response or behavior of the malignant cells of a tumor itself as well as the response of the normal cells proximate to the tumor(s). Further, the present invention allows both real-time treatment information during active therapy sessions as well as dynamic tracking during non-active periods. Indeed, a patient can transmit or communicate the monitored parameters on a regular basis with a clinical site via implantable telemetry based sensing devices and home base receivers (such as even multiple times in a 24 hour period) in a relatively cost-efficient manner. This ongoing communication can download real-time information regarding the state of the tumor to a clinical monitoring station. This information can then be analyzed by computer programs to identify or evaluate oncology treatment strategies associated with a particular tumor type. For example, the dynamic tracking can identify relative changes in the tumor and/or absolute values associated with a positive or negative reaction to therapy. This reaction tracking can allow for more proactive therapeutic decisions based on the tumor's response to the treatment. The dynamic tracking can also be used to identify the onset or predict a potentially vulnerable phase of a tumor to allow more effective timing of treatment regimes corresponding to the actual behavior of the tumor. Preferably, the sensors are positioned at more than one location in the tumor (surface and at a penetration depth), and more preferably at more than one region (over the volume or surface area) associated with the tumor(s) to be able to quantify the tumor's overall response to therapy.

Advantageously, the systems, methods, and devices of the present invention can monitor, in real time and/or dynamically, specific indices associated with tumor physiology making them available for immediate use in treatment decisions. Hence, the instant invention can lead to more definitive and patient-specific treatment protocols, increase tumor response, decrease treatment morbidity, and improve and/or replace assays predicting tumor response, resistance and sensitivity. The present invention can provide information not previously readily available for commercial clinical applications which will likely open new fields of research and therapeutics. The device is particularly suitable for oncology applications.

BRIEF DESCRIPTION OF THE DRAWINGS

FIG. 7 is a side section view of an injectable microsensor according to the present invention.

FIG. 8A is a section view of the sensor shown in FIG. 7 taken along line 8A—8A.

FIG. 8B is a front perspective view of an alternative embodiment of an injectable microsensor similar to the embodiment shown in FIG. 7.

FIG. 9 is a schematic illustration of an implant sensor according to another embodiment of the present invention.

FIG. 14A illustrates capacitor voltage over time, FIG. 14B illustrates control voltage over time, and FIG. 14C illustrates an output voltage waveform.

FIG. 17A illustrates temperature versus pulse width of data corresponding to a thermistor (with the chip inside a water bath of varying temperature). FIG. 17B illustrates temperature versus pulse width of data corresponding to a fixed resistor (also with the chip inside a water bath of varying temperature).

FIG. 18A illustrates pulse width versus radiation of data corresponding to the thermistor with the chip inside the water bath and exposed to radiation from about 0–8000 cGray (a patient is typically treated with radiation in the range of about 3000–6000 cGray). FIG. 18B illustrates the data corresponding to the fixed resistor data with the chip inside the water bath and exposed to radiation from about 0–8000 cGray.

FIG. 19A is a schematic illustration of a subject with monitoring system with two separate and spaced apart implant sensors positioned on two different tumors according to one embodiment of the present invention. The monitoring system receiver can refocus to monitor both locations and transmit the data to a remote location.

FIG. 19B illustrates an implant sensor with four sensor elements in position (in situ in vivo) according to one embodiment of the present invention. As shown, two of the sensor elements are positioned at different surface locations on the tumor, while one of the sensor elements is positioned to penetrate a depth into the tumor. Still another of the sensor elements is positioned proximate to normal tissue that is proximate to the malignant tissue or tumor.

DETAILED DESCRIPTION OF PREFERRED EMBODIMENTS

Figure 1A:
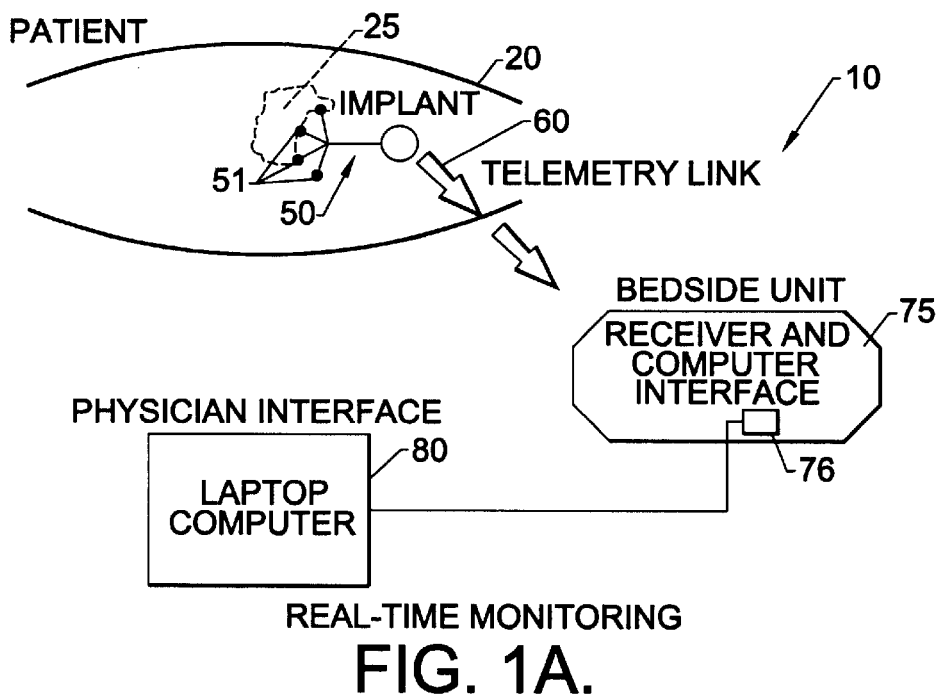
FIG. 1A is a schematic illustration of a tumor monitoring system according to the present invention. The illustration portrays a real-time monitoring capability.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. In the figures, certain layers, regions, or components may be exaggerated or enlarged for clarity.

Generally stated, the systems, devices, and methods of the present invention are aimed at monitoring the changes in physiology and kinetics of living systems. More specifically, the present invention's goal is to monitor at sufficient intervals (preferably semi-continuously, and more preferably substantially continuously) the changes in oxygen, pH, and cell proliferation of any organ or tumor system under "normal" physiological conditions, in-situ, as well as prior to, during and following any perturbation (such as radiation, chemical or cytotoxic stimuli and hyperthermia) of such systems. As such, the monitoring systems and methods of the present invention can be useful in many applications, such as, for example, pulmonary, gastrointestinal, neuroscience and pre-clinical research. Nonetheless, the present invention has a particular importance and suitability to tumor systems. As such, the following description of preferred embodiments will primarily discuss the utilization of the present invention for cancer applications.

As noted above in the Background of the Invention, most conventional cancer treatment strategies employ an empirical approach. That is, the timing and delivery of cytotoxic agents are guided more by the response and toxicity to normal tissue than by the effects on the malignant cell population. Thus, a major deficiency of this empirical approach is the lack of an efficient method or technique to provide accurate information on the dynamic changes during treatment that occurs within a malignant cell population. Making this invaluable information available to attending physicians will allow them to exploit the revealed differences between malignant and normal cells, and hence improve the treatment procedures to achieve better outcomes. Conventionally, the normal tissue surrounding the tumor governs the dose of radiation and the scheduling and doses of chemotherapy is most dependent on the tolerance of the patient's bone marrow. The primary reason for the lack of individualization of treatment is that there is presently no commercially viable means by which the basic information on kinetics and physiology of the tumor can be obtained during and following treatment. A biopsy of the tumor will yield information at one point in time and therefore is valid for only that point in time. This static "snapshot" information may not be valid for predicting the cell kinetics, especially cell kinetics following perturbation by any cytotoxic agent.

There have been a number of attempts to study the dynamic changes occurring within a cell population. However, these lack the ability to monitor the changes on a real time basis. Instead, the conventional methods provide information at one point in time, most are designed to provide information on one function, and most are expensive and time consuming, especially when one considers that it is important to monitor parameters before, during, and following treatment.

The major goal of cancer therapy is to eliminate all tumor cells. Knowledge of the specific change occurring within the tumor at substantially any time can be desirable in order to achieve maximum tumor cell kill and minimum normal tissue damage. Cytotoxic agents are most effective at specific times and conditions of tumor growth. If the most vulnerable time of the tumor cells can be determined, i.e., the time of maximum oxygenation or identification of an increase in cell proliferation associated with phases of the cell cycle, then this information can be used to direct the time of delivery and the choice of the cytotoxic agents.

Preclinical and clinical medicine are in need of information on the dynamic changes which occur in malignant tissue prior to, during, and following cytotoxic (active) therapy sessions in order to define more clearly the circumstances for increasing tumor response. Access to such information can allow for more precise timing of the delivery of cytotoxic agents as well as identifying the most appropriate agent(s), e.g., radiation or chemotherapy therapy. Conventional radiological investigations are limited by their ability to observe dynamic changes, although NMR and PET scan can identify some functional changes. The currently available anticancer agents, although effective in a limited number of tumors, are relatively ineffective in the majority of cancers. The instant invention recognizes that the reasons for this lack of improvement in outcome are typically multifactorial and related in part to an inability to measure, in situ, the time profiles of the most sensitive parameters. These tumor parameters include one or more of, but are not limited to, the degree of oxygenation, pH, cell cycle phases, cell proliferation, and the molecular and cellular determinants of sensitivity or resistance to cytotoxic agents. The present invention recognizes that the availability of such information and the ability to act upon such information can provide the means of overcoming a major barrier to improvements in outcome in cancer therapy. Further, it is believed that this newly provided information can create a shift in the therapeutic paradigm from empirical to individual based therapy which can rely (at least in part) on the molecular and cellular properties of the individual patient's tumor.

Advantageously, the present invention now can provide information on the changes occurring during and after therapy which can be utilized to direct therapy and/or to monitor the effects of the therapy. This individualization of therapy can not only improve outcome but also decrease toxicity and morbidity of the treatment. That is, the information obtained on each patient's tumor can radically change the scheduling of therapy and result in an improved outcome. For example, patients can now be monitored from home, through telephone lines or some other remote interface, to determine a favorable or most appropriate time for treatment.

Thus, as noted above, the present invention is primarily directed to the in vivo evaluation and monitoring of tumors prior to, during, and subsequent to an active treatment, and preferably over an entire treatment regime or period. That is, the present invention is particularly suitable for monitoring the behavior of cancerous tumors such as sarcomas and carcinomas over a particular non-remission treatment period. As such, the internal in situ sensors of the present invention are preferably configured to be biocompatible and provide a service life suitable for episodic treatment evaluation of at least about 4–6 weeks, and more preferably at least about 6–10 weeks, and still more preferably at least about 10–12 weeks, whether exposed to radiation, chemotherapy, heat or ionic electric fields (such as the treatment provided by a Thermotron®) directed to the tumor. The sensors and preferred tumor monitoring parameters will be discussed further below.

Turning now to FIG. 1A, a real-time tumor monitoring system 10 is illustrated. As shown, the tumor monitoring system 10 includes an in situ sensor unit 50 positioned in a subject 20 proximate to a tumor 25. Preferably, as is also shown, the sensor unit 50 includes a plurality of sensor elements 51 positioned at different locations on and/or into the tumor 25. It is preferred that the sensor elements 51 monitor more than one physiological parameter or a selected physiological parameter associated with the tumor at more than one position in, on, or about the tumor as will be discussed further below. The sensor unit 50 is configured with a telemetry link 60 to wirelessly communicate with an externally located receiver 75. The receiver 75 includes a computer interface 76 and is operably associated with a physician interface module 80 such as a display monitor associated with a central processing unit, computer, or other computer means to allow physician access to the monitored data. As shown, the physician interface 80 is a laptop or other mobile/portable computer means to allow a physician instant access to the substantially real-time monitored tumor parameters.

Figure 2A:
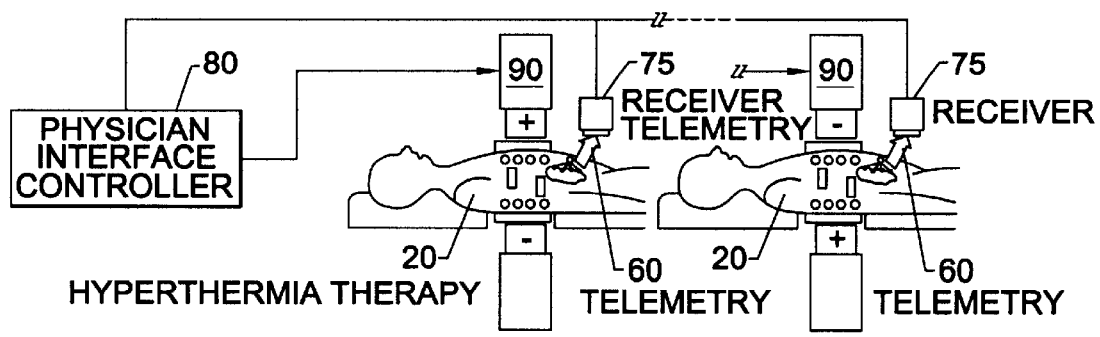
FIG. 2A is a schematic diagram of a tumor monitoring system configured to relay real time tumor information during an active treatment session (shown as an electric field treatment therapy) according to one embodiment of the present invention.
Figure 2B:
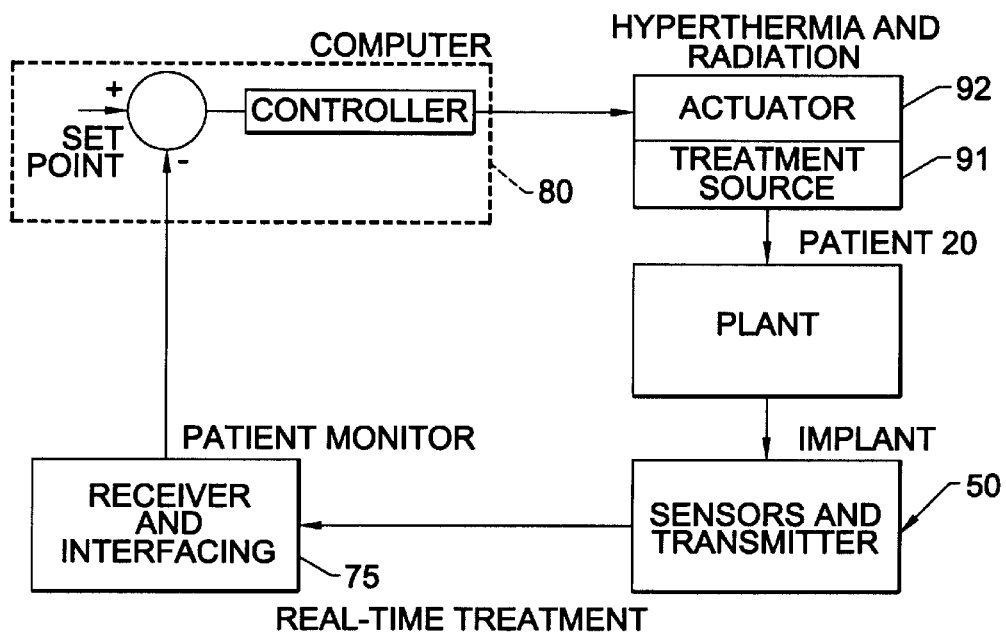
FIG. 2B is a block diagram illustrating a tumor monitoring system configured to relay information (real-time) during a hyperthermia and radiation treatment session.

FIGS. 2A and 2B illustrate exemplary applications of real-time evaluations according to the present invention. FIG. 2A illustrates using the monitored parameter(s) of the tumor during a hyperthermia therapy session (such as via Thermotron® device) to control the length, power, field strength, or polarity of the treatment. This control can be provided because the real-time monitored data associated with at least one tumor parameter can provide feedback on the actual treatment penetration depth (via temperature or other parameter) at the tumor itself. Alternatively, the information regarding the condition or behavior of the tumor may suggest another treatment would be more beneficial, or even that further treatment would not be beneficial (at that time). Indeed, it is preferred that prior to initiation of any active treatment, the tumor data is monitored to assess whether conditions are favorable or indeed, unfavorable, for the treatment strategy proposed. That is, if a drug therapy is recommended for tumors exhibiting a pH above a certain value, and the data suggests that the tumor pH is below this value, a physician may choose to postpone that particular therapy for a more favorable time. Of course, other parameters, such as an elevated oxygenation level and a phase of increased cell proliferation, may suggest that other therapy would be more advantageous or that the drug therapy should nonetheless proceed. Additional discussion regarding tumor parameters and the relationship to treatment is provided below.

FIG. 2B illustrates the use of the real-time tumor data in a control feedback loop to control one or more of the power, dose, or duration of a hyperthermia and radiation treatment session. As shown the monitored transmitted data is sent to the receiver, 75 which then inputs the data into a computer which has a controller directing the actuator 92 and treatment source 91 (which directs the treatment into the patient). The patient 20 is noted as the controlled "plant" in this figure.

Figure 1B:
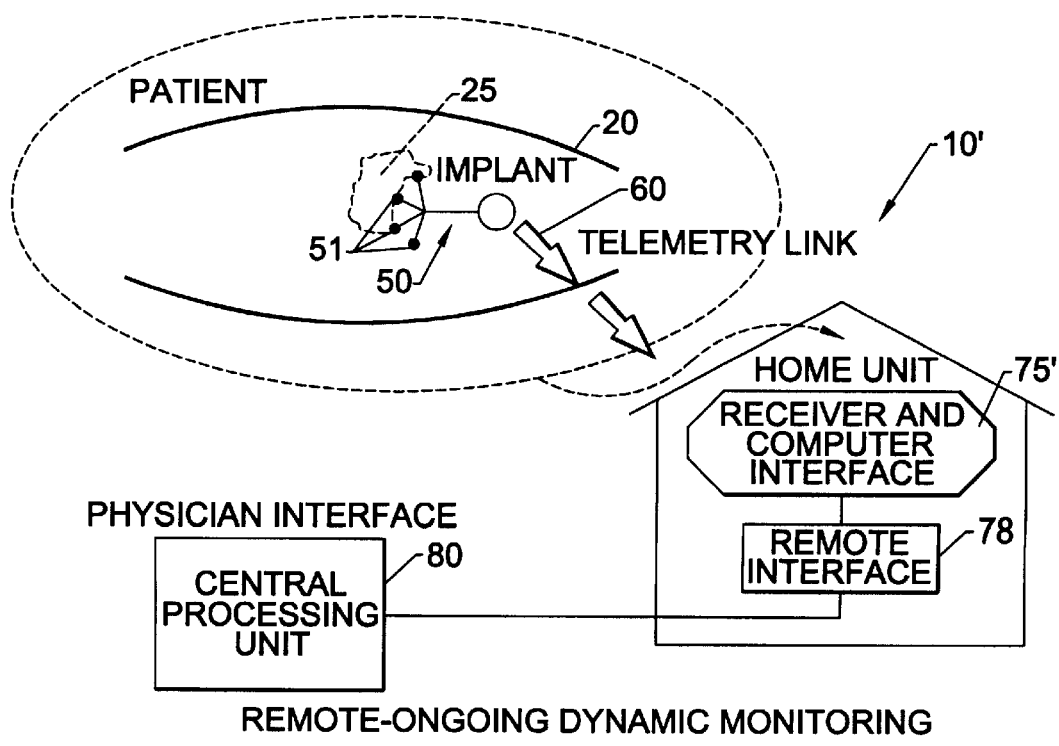
FIG. 1B is a schematic illustration of an alternate tumor monitoring system according to the present invention. This figure illustrates an ongoing dynamic remote monitoring capability.

FIG. 1B illustrates an alternate embodiment of a tumor monitoring system 10'. In this embodiment, the tumor monitoring system 10' includes a home receiver unit 75' and a remote interface 78 which communicates with the physician interface 80 (the physician interface shown in this embodiment is a central processing unit). The patient 20 (the dotted line represents the patient being in the house proximate to the receiver 75') even when at home can continue to monitor and transmit data to a remote site. The remote interface 78 can provide the communications link between the monitored local data and a remote clinical oversight station. As such, the remote interface 78 can be provided by any number of interface or data load means including a computer modem, a wireless communication system, an internet connection, or telephone connection. In this embodiment, upon identification of the existence or onset of a favorable condition for treatment, the central processing site can automatically schedule an evaluation appointment or even schedule a treatment session on therapeutic equipment to take advantage of an opportune or favorable treatment window(s).

Figure 3:
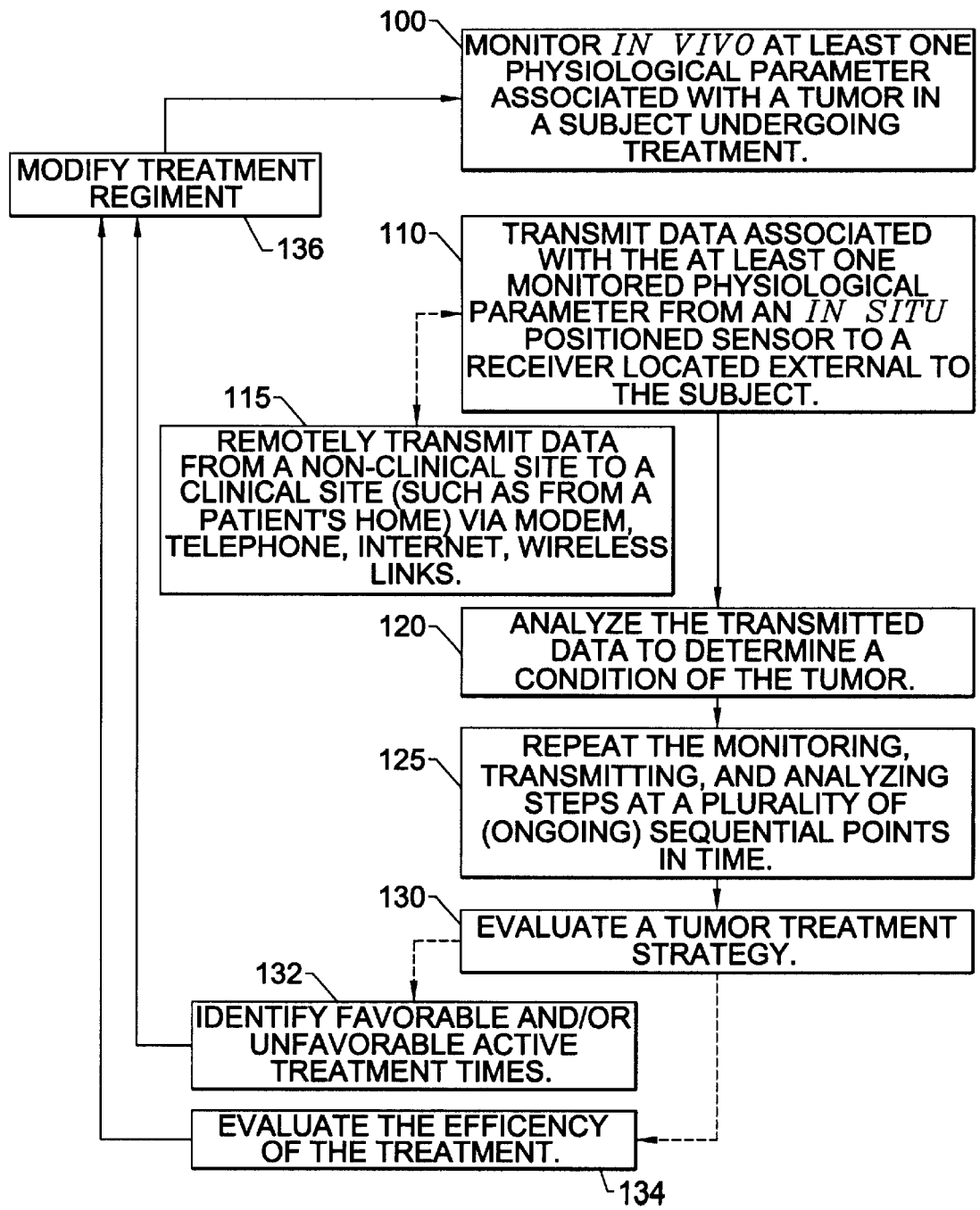
FIG. 3 is a block diagram of a method of monitoring a tumor undergoing treatment according to the present invention.

FIG. 3 illustrates a preferred tumor monitoring and treatment evaluation method according to the present invention. At least one (and preferably a plurality of) physiological parameter associated with a tumor in a subject undergoing treatment is monitored (Block 100). Data associated with the at least one physiological parameter is transmitted from an in situ positioned sensor unit 50 to a receiver 75 located external to a subject (Block 110). The data transmission can be remotely transmitted from a non-clinical site (such as at a patient's home) to a clinical site via modem, telephone, wireless communication systems, and the like (Block 115). The transmitted data is then analyzed to determine a condition of the tumor (Block 120). The monitoring, transmitting, and analyzing steps are repeated at a plurality of sequential points in time (Block 125). That is, as opposed to a "static" single point in time data point, the instant invention allows dynamic monitoring (a plurality of sequential points in time). The dynamic tracking to variation in the tumor can yield valuable therapeutic and diagnostic information. The data is transmitted on a periodic basis (such as every 4–24 hours) over a particular treatment period. The data is transmitted in an at least an intermittent manner (although the data may be transmitted in less or more frequent data transmissions) during an entire treatment cycle, typically from about 1–3 months. More preferably, the data is substantially continuously or semi-continuously monitored (every 1–60 minutes, and more preferably every 1–30 minutes) and, at least locally, transmitted. This ongoing (intermittent, semicontinuous, or substantially continuous) monitoring allows the dynamic tracking or monitoring of the physiological parameter(s).

Of course, the continuous or semi-continuous monitoring/transmitting can be performed locally for electronic storage within memory associated with the receiver/computer interface 75' and then subsequently transmitted (to a central monitoring site on a less frequent basis, such as hourly, daily, and the like). It may be beneficial to preset a data transmittal/acquisition time via a timer in communication with the receiver 75' corresponding to a physician's input (e.g., more frequent monitoring closer in time to the introduction of cytoxic agents or pertubation, such as every 1–5 minutes, with less frequent monitoring subsequent thereto, such as every 10–15 minutes, or hourly). Alternatively, the data monitoring/transmitting or acquisition time may be self-adjusting and relatively set such as by comparing and reviewing the transmitted data periodically to determine rates of change upon which to institute a more frequent assessment, then transmit less frequently during times of less change in the values. In any event, for stationary receiver units 75, 75', the patient needs to be in proximate position with the receiver 75' to facilitate proper data transmittal. In order to facilitate the proper position of the patient for a subsequent transmittal to the receiver 75', the receiver 75' is preferably configured to generate an alert or alarm when a desired monitoring transmittal time is approaching. This can remind a subject to approach the receiver for proper transmission therebetween. Of course, the receiver 75' can be programmed to audibly state the next transmitting time based on the values of the most recently transmitted data while the more current transmittal is still underway (or on the change between a series of more recent transmittals).

In an alternative embodiment to the home-based tumor monitoring system 10' shown in FIG. 1B, the receiver 75' can be configured to be portable and sufficiently, light weight to allow a user to wear it (attached to clothing or other supporting belts or suspenders or the like) such that it is in a desired proximity to the imbedded sensor unit(s) 50 to more easily provide semi-continuous or substantially continuous dynamic data tracking. Preferably, the portable receiver unit (not shown) is self-powered with a trickle charger (to plug into a vehicle accessory power source or a wall outlet in the home) to allow a user to recharge the unit when not mobile. It is also preferred that the portable unit be configured with sufficient memory to be able to store a block of data over a period of time before uploading to the remote interface, or directly to a computer interface at a clinical site.

In any event, referring again to FIG. 3, a tumor treatment strategy can be evaluated based on the dynamic information provided by the monitored parameter(s) (Block 130). This evaluation can result in a verification of the efficacy of a treatment (Block 132) such as, for example, to determine whether the tumor is responding or resistant to the treatment. Further, the evaluation can verify that a given active dose was received at the tumor and in what amount. One example is to quantify the amount of radiation seen or received at the tumor (this can be helpful if the tumor is blocked by dense tissue or is irregularly configured or positioned in the body in hard to reach regions). This verification may also be particularly suitable for use with newer targeted drugs which are designed to target the specific treatment zone in the body. This verification can thus affirm that the drug is delivered to the region intended.

In addition, the evaluation can be advantageously used to identify either, or both, of the presence of a favorable or unfavorable treatment time (Block 134). For example, if conditions indicate the tumor is not receptive to the planned treatment, a change in the planned therapy can be promptly instituted, or, in the reverse, the resistance can result in a rescheduling of a planned therapy to a more favorable time, thereby minimizing exposing the subject to unnecessary therapy sessions at unfavorable times. In addition, the therapeutic evaluation can be based on either or both of relative or absolute parameter values (or indeed a clustering of irregular, positive, or negative parameter values) to determine if the treatment is progressing according to a predictive model. The predictive model can be based on the deviation of the tumor's response to the delivered therapy at a particular point in time as measured against a population norm or even against a historical perspective of the patient's own responses to previously delivered therapies. This can allow a physician to choose (or modify) the therapy for a subject based on the responsiveness of the tumor itself. Thus, the information can result in modification of the planned treatment regime (Block 136). For example, for discussion purposes, assume that at Day 3 from a chemotherapy type and dose, the tumor oxygenation is low, and the normal cell's susceptibility to toxic agents is high. In contrast, assume that at Day 3, the tumor oxygenation is high, and the normal cell's susceptibility to toxic agents is low. In the latter, this behavior may be according to a predicted outcome or an unpredicted outcome; if unpredicted, one might proceed to schedule take advantage of the favorable conditions for treatment and schedule an additional therapy session promptly (i.e., a favorable active treatment time). If predicted, then the planned therapy can proceed as scheduled.

Determining Tumor Physiological Parameters

It is generally well accepted that tumor oxygenation and blood flow are important to the efficacy of most types of cancer therapy. Hypoxia (low oxygen) and thus radiation resistance occurs in poorly perfused regions of tumors (Gray et al., 1953). In addition, anticancer drugs of all kinds gain access to tumor cells through blood vessels, and poorly perfused regions also hinder drug delivery (Jain et al., 1988). For these reasons, there has been great interest in developing methods for modifying and monitoring tumor blood flow and oxygenation, primarily to find ways to increase radiation sensitivity. However, a knowledge of tumor oxygen levels can lead to alternative approaches, e.g., hyperthermia effects which are enhanced in hypoxia (Stratford et al., 1994). More recent information on the influence of hypoxia in the regulation of genes and cytokines has continued to stimulate interest in this area (Sutherland et al. 1994)). Further, it is likely that these effects are involved in influencing patterns of metastases (Young et al., 1997), angiogenesis (Schweiki et al., 1992) and drug resistance (Sakata, 1991).

Currently there is no commercially feasible clinically applicable noninvasive method of assessing tumor hypoxia (McCoy, 1996). Magnetic resonance imaging and positron emission (Robinson, 1998) have been discussed as possible means to monitor changes in tumor perfusion and blood oxygenation. However, these methods are cumbersome to monitor the daily and dynamic changes, which occur during the perturbation of a tumor. The ability to monitor tumor oxygenation and changes within the tumor during various challenges is important to improve cancer therapy. The information obtained can direct the type of and timing of appropriate therapy, in order to increase the cytotoxic effect.

A substantial body of evidence has accumulated over the past 50 years indicating that electrode-evaluated human tumor pH is, on average, lower than the pH of normal tissue. However, strategies to explore this difference have been hampered for two reasons; first, overlap of electrode-measured tumor and normal tissue pH, especially when data is pooled. Second, more recent demonstration using 31P magnetic resonance spectroscopy (MRS) indicates that tissue pH can be divided into two compartments: intracellular and extracellular—(a) pH determined by electrodes primarily measure interstitial or extracellular pH and (b) pH determined by MRS primarily reflect intracellular pH ("$pH_i$"). Moreover, the $pH_i$ of normal and tumor tissue is similar whereas the extracellular pH may vary significantly between normal tissue and tumor and tumor of the same origin but in different patients. For example, the range of pH in breast tumors has been demonstrated to be from 6.85–7.5 and in the subcutaneous tissue of normal volunteers it was from about 7.3–7.9.

The electrode-measured pH of tumors is on average 0.4 units lower than normal subcutaneous or muscle tissue. Although overlap between normal and tumor tissue may exist, they may be explained by technical and patient-related factors. However, the present invention recognizes that measuring pH in both normal and tumor tissue at the same time and on a continuous basis can eliminate this variation. The ability to accomplish this can enable the physician to exploit the differences. Since the acidity increases with increasing distance from the supplying vessel and $pH_i$ is similar in each tissue, the intra to extra cellular pH gradient may be expected to increase in those cells most distal from blood vessels. The overall effect would be to enhance drug uptake and killing of cells that are normally exposed to the lowest drug concentration and especially relevant to radiation therapy in which low oxygen concentration—and therefore radiation resistance—increases with increased distance.

Accordingly, in one embodiment of the present invention, the sensor unit 50 (whether self-powered and implantable or injectable with an inductive powered version as will be discussed further below) can be inserted into the tumor(s) and secured therein or thereto in order to gather information, preferably for a number of weeks as discussed above. As shown in FIG. 19B, the sensor elements 51 are configured such that they are placed at different levels and in different locations in the tumor. It is also preferred, as is also shown in FIG. 19B, that at least one sensor element be configured to monitor the treatment toxic affect or normal cells and/or the pH level of the normal cell tissue proximate the tumor.

It has been shown that a difference in oxygen levels exist between tumor feeding arterioles (about 32 mm Hg) as opposed to the about a 50 mm Hg level in healing or normal tissues. And as noted above, low oxygen levels leads to treatment resistance in a tumor cell. If it is determined, with the aid of the device, that the majority of the tumor is hypoxic (i.e., less than 50 mm Hg, and preferably less than about 40 mm Hg, and more preferably about 32 mm Hg or less), then it should not be treated until the oxygenation of the tumor is improved. This can occur in several ways. The tumor can be heated (hyperthermia) which works best in hypoxic conditions and which may eliminate enough cells to make the remaining population less hypoxic, or the tumor can be exposed to specific drugs to improve the oxygen concentration. The important point is that the tumor is not treated until more cells are oxygenated and, therefore, more sensitive or vulnerable to the conventional active treatments of radiation or chemotherapy. Similarly, the sensitivity and, therefore, cell kill of malignant cells can be affected by pH and cell proliferation. pH measurements of the tumor tissue would be important as the pH can influence not only the delivery and uptake of drugs, but also affect the oxygenation of the tumor. Therefore, if it is determined that the pH of particular tumor is 7.2 and the uptake of the drug of choice is undesirably affected by a pH greater than 6.9, then the drug should be withheld and the pH changed. Cell proliferation can be measured with the aid of a beta radiation sensor able to monitor uptake of any radioactive tagged substance or ligands and provide information on cell kinetics and proliferation. If the uptake of a particular ligand which measures for cell proliferation is high (indicating active cell proliferation and therefore increased sensitivity), then the drug or radiation should be delivered.

It will be appreciated by those of skill in the art that at this time, specific dynamic changes and/or values of those changes occurring in pH or oxygenation of cell proliferation during and after treatment have not been definitively quantified (but which can now be established based on the dynamic monitoring provided by the present invention). Further, the pH, cell proliferation rate and schedule, and oxygenation can vary significantly from patient to patient, even within patient groups having the same type of tumor. Indeed, it is believed that this variability can account for the difference in response from patient to patient when treated with the same drug. Why should only 10, 20, or even 30% of patients respond to a drug that, according to in vitro data, should produce a tumor response of greater than 50%? Advantageously, the present invention will now allow data to be collected on specific values of for each monitored parameter or variable (preferably including pH, oxygen tension, and cell proliferation) during and following cytotoxic treatment. The collected data can be studied and a specific set of variables identified to affect a particular response. Armed with this information, a patient can be more effectively treated. Thus, the present invention will now allow not only the establishment of specific variable information for evaluation, but, can also be used to direct and monitor the effects of treatment.

Thus, in a preferred embodiment, the present invention configures a tumor monitoring system with sensor elements designed to monitor one or more of tumor pH, oxygenation level, temperature, and cell proliferation. The cell proliferation can be measured presently by the use of a radiation sensor (which can also be used to verify the dose of radiation received at the tumor during radiation therapy). It is anticipated that other biochemical or biomolecules will be determined to be sensitive indicators of the vulnerability of the tumor for treatment and, thus, useful according to the present invention. The present invention can provide all these sensors in each tumor, gathering and transmitting the information in real time, to a computer containing an algorithm to process the information to determine if and how the patient is to be treated.

Figure 4:
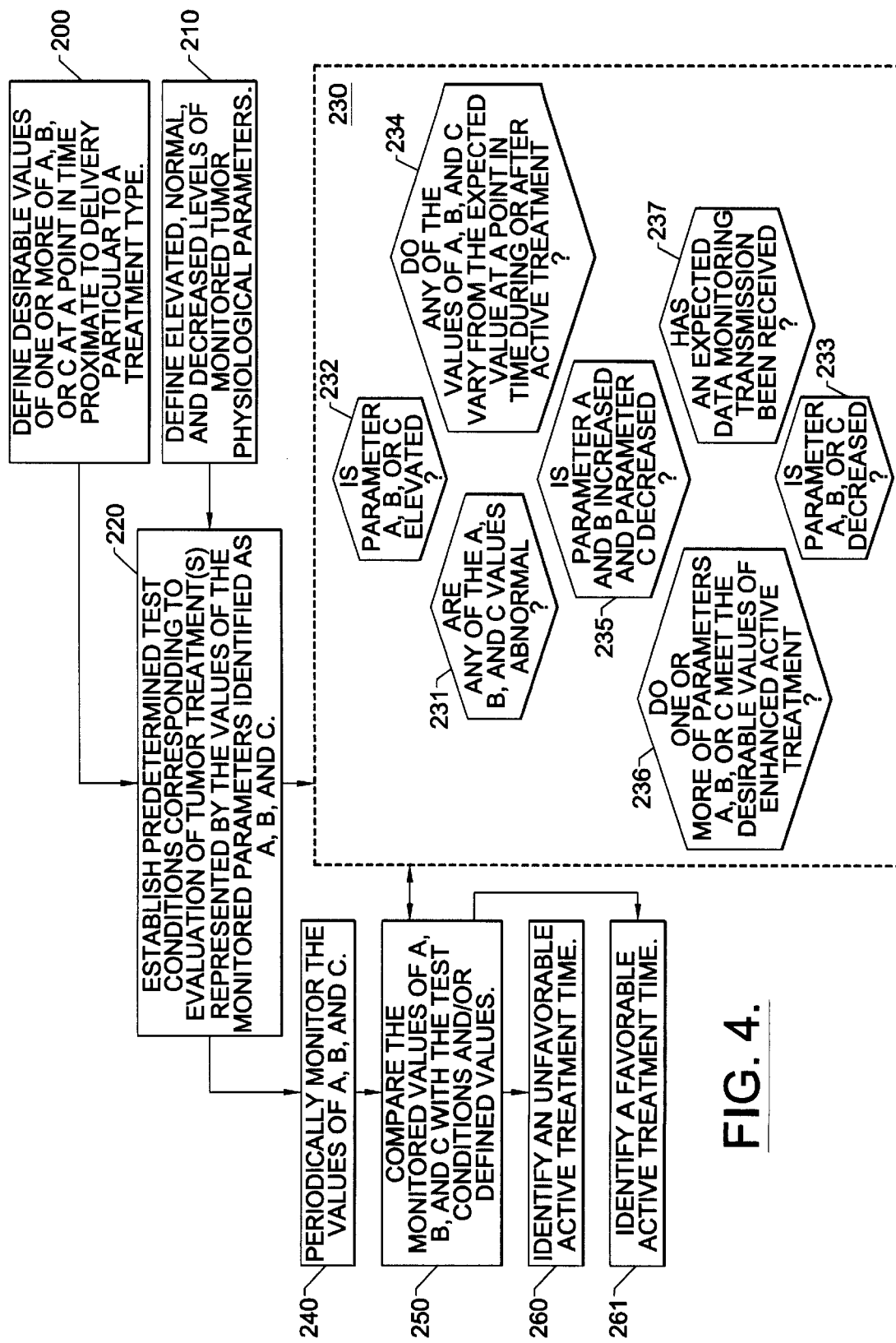
FIG. 4 is a flow chart of a method to identify favorable and unfavorable treatment times according to the periodic (dynamic) monitoring of a plurality of tumor physiological parameters according to the present invention.

Turning now to FIG. 4, an exemplary data analysis method is illustrated which evaluates and analyzes the data associated with the monitored parameters. As shown, the desirable values of selected physiological parameters (shown as at least three parameters A, B, and C) are identified or defined as they relate to the desired condition proximate to an active therapy (Block 200). The desirable values for each of the parameters may be input as a minima or maxima and may be cross-related to a particular treatment type. That is, one parameter, for discussion identified as parameter "C" (such as pH), may require or desire a certain minimum or maximum value to achieve maximum effectiveness particular to a certain treatment type (such as a particular chemotherapy or drug treatment). In contrast, another parameter, for discussion, identified as parameter "A" (such as oxygenation level) may have the same preferred value across all treatment regimes (typically a minimum value as a normal or an elevated oxygenation level is desirable). As such, if there is a minimum or maximum value at which therapy should not proceed, it is identified as a test criteria for data analysis just prior to the delivery into the subject of the treatment.

Similarly, a range of physiological parameter values particular to the parameter can be used as a basis for test criteria; for example, defining the levels associated with "elevated," "decreased" and "normal" can be input (Block 210). This criteria (as well as relative levels, population norms, or other indices of tumor behavior and treatment efficacy) can then be used to define test conditions corresponding to evaluation of tumor treatments (Block 220). That is, the test conditions can be any number of tests representing evaluation of the tumor and the treatment. As shown, the test conditions also test for abnormal values of the monitored parameters (Block 231). This can identify the malfunction of a sensor, sensor element, or other component of the monitoring system as well as identify a potentially immediate need for medical evaluation. Other test conditions can include testing for elevated or decreased parameter values (Blocks 232, 233) respectively. Similarly, the presence of a clustering of "favorable conditions" represented by two of the parameters having increased or elevated parameter values and another having a decreased parameter value (Block 235) may represent a more favorable treatment period. For example, the presence of an elevated oxygenation level together with a period of increased cell proliferation and a decreased pH level may trigger a favorable treatment window. Of course, the clustering of just the two increased parameters can also be a test condition. In addition, one test condition can review the parameter values to determine variation from an expected value based on a predictive model (statistically relevant variation from a relative reaction or from a population norm) based on a point in time during or after active treatment (Block 234). A test condition which identifies whether the parameters meet the defined desirable values may also be helpful (Block 236). It may also be beneficial to have a test to determine if an expected data monitoring (local and/or remote) has been received or is missing (Block 237). This could indicate data corruption, file corruption, or even be used to automatically call the subject (such as with a programmed or recorded telephonic message) to notify them that a data transmission is needed.

In any event, the physiological data is periodically monitored (Block 240) and the data is compared to the test conditions/defined values (Block 250). An unfavorable active treatment time and a favorable active treatment time can then be identified (Blocks 260, 261), respectively. Of course, other evaluations and therapy decisions can also be made. The favorable test time can be identified by the test conditions/parameter values indicating a positive indicator (favorable condition or good progression). Of course, the data may also reflect a norm indicator (neutral condition), and a negative indicator (unfavorable condition or resistance to therapy). It is envisioned that a global network database or a regional database associated with each hospital or clinical site identifying the appropriate values can be pre-established to minimize-the data input needed for a particular subject.

It will be understood that each block of the block diagrams (or block in the flowchart illustrations), and combinations of blocks in the flowchart illustrations or blocks in block diagram figures), can be implemented by computer program instructions. These computer program instructions may be loaded onto a computer or other programmable data processing apparatus to produce a machine, such that the instructions which execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce computer implemented process such that the instructions which execute on the computer or other programmable apparatus provide steps for implementing the functions specified in the flowchart block or blocks and/or block diagrams.

Accordingly, blocks of the block diagrams or in a flowchart illustration support combinations of means for performing the specified fuctions and program instruction means for performing the specified functions. It will also be understood that each block of the block diagram or flowchart illustrations, and combinations of blocks in the block diagrams or flowchart illustrations, can be implemented by special purpose hardware-based computer systems which perform the specified functions or steps, or combinations of special purpose hardware and computer instructions.

Although the present invention will likely provide additional basis for establishing more definitive numbers or values for monitored tumor physiological parameters, the following parameters and levels and indicators are provided as suitable for establishing test criteria associated with treatment or tumor condition.

Conventional treatments use combination therapies such as temperature and radiation (tumor heated twice a week while irradiating every day).

Temperature

One approach to the treatment of large unresectable tumors is the use of radiation and thermal treatment. Typically, in such instances, the tumor is irradiated daily and heated twice per week following the daily radiation treatment. The temperature range preferred to achieve an increased, and hopefully maximum, cell kill is between about 42–43.5° C. This temperature is then preferably maintained for about 20 minutes. The temperature is monitored closely to minimize the effects on the surrounding normal tissues and to assure that the same temperature is substantially homogeneously obtained throughout the tumor. This treatment technique is utilized and found to be effective for primary tumors from a number of tumor sites, including, but not limited to, the lungs, the prostate, the breasts, melanoma, the pancreas, and the pelvis. Thus, the present invention can provide an easy and effective thermal monitoring means by which temperature can be monitored, the thermal monitoring can prove especially suitable for externally inaccessible tumors or for tumors located deep within the body, which are not easily monitored by conventional means.

Level of Oxygenation

The oxygenation level need to overcome radiation and or chemotherapy resistance has not been definitively established on dynamic systems as noted above. That is because, the precise changes which occur during treatment have not been quantified and therefore it is difficult to predict what definitive value may ultimately be established as necessary to overcome radioresistance now that dynamic monitoring protocols are available. This information will be obtained upon clinical applications of the proposed invention along with specific correlation with treatments and responses. Ultimately, lower oxygen tension may be found to be effective for treatments and that a normal or elevated oxygenation is not required for successful treatment. Nonetheless, the current preferred treatment approach is to achieve at least as normal a level as possible (and not to deliver during decreased oxygenation periods). Accordingly, for reference, the term "elevated" can be described as levels above 52 mm Hg. The term "normal" can be described .as levels from about 50–52 mm Hg. While the term "decreased" can be described as levels at or below 49 mm Hg, and more preferably, below about 40 mm Hg. It should be noted that oxygen is important for most, if not all tumor types, and is not specific to one type of tumor (although a particular level may be more suitable for treatment of one type). Further, in situ sensors according to the present invention can be positioned at different positions within the tumor to monitor the distribution of oxygen. If a significant difference (or delta) is detected, an attempt can be made to increase the oxygen levels to a sufficient level across the tumor.

Accordingly, the radiation or chemotherapy treatment can be withheld and given only when the oxygenation level approaches a minimum of about 50 mmHg or is within a range determined to be appropriate for that patient (based on a relative response and/ or absolute response data).

Cell Proliferation

As noted above, cell proliferation is an important property of malignant tumors which can effect outcome. A knowledge of the time during which the tumor cells are proliferating is important in order to achieve a greater cell kill, and in turn, a greater response to therapy and an improved outcome. The degree of cell proliferation is related to the number of cells, which are cycling. Thus, if a ligand associated with cell proliferation is tagged, it will be incorporated into cycling cells and reveal itself as increased radioactivity within the tumor. Under normal or quiescent conditions, only about 2–5% of cells are typically cycling. This quantity will increase generally by an order of magnitude to 20–25% in a moderate or highly proliferative state. The difference in uptake of the radioactive material will be noticeable and can be correlated to periods of increased cell proliferation. The time during which this increased proliferation is not readily known and has not been readily identifiable. The time during which cell proliferation occurs may vary with the specific tumor type, as well as the rate of proliferation itself (the time it takes to double the population).

Tumor pH

The pH of tumors has been found to be lower (more acidic) than the pH associated with normal tissue. The precise pH or range of pH needed for maximum effect is not known, nor have the fluctuations encountered during treatment been quantified as noted above. The impact of information regarding pH can be more complicated than that oxygen since pH may effect oxygen level, drug uptake, and cell proliferation. In addition, surrounding normal tissue can also effect the tumor pH. At present, it appears that a more acidic environment (pH of between about 6.8–7.0) may be preferably for treating malignancies. This is based on in vitro data which indicates that at least one drug, adriamycin, is more effective at low pH. As also noted above, the difference in pH between normal and malignant cells can be narrow (about 0.4 units) and therefore may indicate that there is a narrow treatment range at which drugs and radiation are more effective. As noted above, the present invention can now determine, in real time, the changes that occur during and after cytotoxic therapy.

Radiation

Radiation monitoring can be used to identify cell proliferation above (typically beta radiation). Radiation sensors can also be used to verify irradiation doses delivered during photon irradiation treatment (typically in the range of between about 3000–6000 cG). Thus, use of a radiation monitor during real time delivery can help control a more precise delivery dose of gamma radiation to the tumor site (distribution of dose within the tumor following photon irradiation or verification of calculated dose, especially with high dose conformal therapy). $\beta$ radiation monitors can also monitor radioactively labeled compounds to monitor drug uptake and utilization, blood flow the tumor, sensitivity to specific drugs, drug distribution in various organs (as well as cell proliferation discussed above).

In summary, a number of tumor (and proximate normal cell) parameters can be monitored, each of which can provide information material to the treatment and condition of a tumor in a subject. Individual parameter combinations thereof, and biomolecular tumor parameters yet to be identified may also be monitored according to the present invention.

Biotelemetry and Implantable Sensors

It will be appreciated by one of skill in the art that when a foreign object is implanted into the body, a series of host responses occur: 1) deposition of blood plasma proteins, 2) fibrin formation, 3) assault by immune cells and proteins, 4) attack by inflammatory cells, and 5) formation of a cellular capsule around the object (Reichert et al., 1992). Therefore, it is important that the materials used in an implanted device address this host response. Much is known about the implantation of sensor systems. Kapton® polymers have been shown to be relatively benign when used as a sensor substrate (Lindner et al., 1993). Pacemaker companies frequently use titanium cases with medical grade epoxies and silicone rubber to encapsulate the external lead connections (Webster, 1995). Implantable glucose sensors have been constructed using polyethylene cases covered in Dacron velour, with the sensor surfaces being coated with a variety of bioprotective membranes (Gilligan et al., 1994). (These units were wet sterilized in 0.05% thimerosal for 24 hours before being implanted and tested in vivo for up to three months.) A more common method used for sterilizing implant devices is gas sterilization at temperatures of 115° C. to 120° C. for 20 minutes.

Early researchers used discrete components to implement simple oscillator circuits for implantable sensors (Mackay, 1995). In recent years, the focus has been on miniaturization, using hybrid and integrated circuits for the electronic portions of the systems. Because the demand for "high-tech" biotelemetry systems in the past has been small, few suppliers have invested resources into developing state-of-the-art systems and devices. Most of this development has been performed at academic institutions around the world, with an emphasis on creating smaller, more-efficient telemetry and telemetry-like devices with increased functionality.

Integrated circuit (IC) technology has been used significantly for biotelemetry device electronics throughout the past two decades. In the mid 1970s, IC usage was made feasible through the use of hybrid technology. This technology enabled engineers to construct telemetry devices by interconnecting commercially available ICs, simple custom ICs, and other discrete components, on ceramic substrates through the used of thick- or thin- film technologies (Fryer et al., 1973; Deutsch, 1979; Gschwend et al., 1979; Donald et al., 1981). Perhaps the best example of this technology is a unit perfected at NASA Ames (Hines et al., 1995). NASA uses a carrier of 455 kHz and digital PCM. The implanted unit is fabricated using hybrid technology and monitors pH, heart rate, temperature, and battery voltage. Its current consumption is less than 120 microamps drawn from a 0.75 A-hr lithium battery. The battery lifetime is 6–9 months. The unit is packaged in a custom-manufactured, diskshaped ceramic package, approximately 3.0 cm in diameter occupying a volume of 20 cc. The telemetry link has an acquisition range 12 to 24 inches.

As the microfabrication processes improved, telemetry units could be fabricated on individual silicon substrates only millimeters in length and width. Recently, biotelemetry systems have been appearing with custom integrated circuits as a major component (Oshima et al., 1987; Williams et al., 1994; Wouters et al., 1994; Akin et al., 1995). In a typical example (Puers et al., 1993), an intelligent 4-channel unit was designed and fabricated for animal husbandry studies. The electronics used for this device were created on a 4.7×7.1 $mm^2$ silicon substrate and included both analog and digital signal conditioning electronics to process the incoming signals, transmit them accordingly, and direct power to the appropriate sub-circuits when needed. As with most IC based transmitters, a few external devices were required for operation, including capacitors and crystals for driving the IC oscillators, accelerometer and temperature sensors, and resistors and switches to set gains and identification codes. It is important to note that such additional components can be undesirable, since they can add to the physical size of the electronics and increase the overhead involved in fabrication. They do, however, give the user/designer more flexibility in modifying circuit operation.

A novel implantable telemetry system was recently under development at North Carolina State University (Fernald et al., 1991 and 1992). The system was intended for rapid-prototyping applications, and was designed such that a nonengineering researcher could construct a customized implant device with minimal effort. The system consisted of two core intelligent integrated circuits, a microprocessor/telemetry chip and a data acquisition chip that could be stacked upon one another and fully interconnected with less than ten bus wires. Although the data acquisition chip provided eight input channels, additional channels could be attained by stacking additional such chips and attaching them to the bus lines in a daisy-chain manner. The microprocessor was fully programmable (both before and after implantation) and possessed an instruction set suitable for processing biological signals. The system was intended for a variety of transducers with varying bandwidths. As a consequence of the serial bus architecture, the system throughput was limited to an aggregate bandwidth of 20 kHz, suitable for most applications.

Researchers have long sought methods to eliminate the batteries in implanted devices (Hansen et al., 1982). Inductive power coupling has received attention in recent years. One research group (Benedetti, 1995) developed an inductively powered implant with four channels for measuring pressure and EMG. The sampling rate was 200 Hz/channel; its size, 15×19×86 mm$^3$; and its weight, 55 g (40 g is the housing). The implant was mounted in a gold-plated brass housing. Surface mounted components were attached to stackable printed circuit boards. The internal power sources were +3 V and −3 V, derived from a power carrier frequency of 27.1 MHz. Current consumption was 6 mA. The transmission/coupling range was 30–70 mm. The telemetry links were sampled FM with a frequency range of 36 kHz–120 kHz.

A second example system incorporating inductive powering was designed for orthopedic measurements (Graichen et al., 1991 and 1995). This unit implemented eight telemetry channels (6 for strain sensing, one for temperature, and one for power supply voltage). The electronics module was a thick-film hybrid substrate with custom IC and discrete components. The substrate was encapsulated in a titanium cylinder measuring 8 mm in diameter and 27 mm high. The telemetry links operates using pulse-interval modulation with a carrier frequency of 150 MHz. The operating range is 20 cm. The implant is inductively powered through a 4 kHz coupling channel.

Inductive powering is also finding applications in cardiovascular and neural studies. A novel 3D power steering scheme has been proposed for high-data rate cardiac mapping studies (Mueller et al., 1995). Researchers have also implemented inductive powering in some telemetry-controlled neural stimulators. Their size has been greatly reduced, allowing them to be injected into tissue through a hypodermic needle. Two such devices have been reported by researchers at the University of Michigan (Akin et al., 1990) and the Illinois Institute of Technology (Loeb et al., 1991). Both systems rely on micro coils and magnetic induction to power the devices, thus eliminating the size and weight associated with batteries. The inductive links were also modulated to convey command information to the implants. Further reduction in size was achieved through CMOS integrated circuit technology. Both research groups proposed incorporating reverse communication capabilities, so that the implanted devices can also perform telemetry monitoring functions (Nardin et al., 1995).

Commercial manufacturers have been successful in building and marketing a variety of models. These systems only have a few channels and are tailored for animal research. For example, Data Sciences International (St. Paul, Minn.) offers a number of models. Their systems use pulse-interval modulation, a low power consuming technique. However, their systems typically use a single carrier frequency per channel, limiting the number of channels that might be implemented. The low input impedance of their electronics also limits the possibility of including pH and other ion-selective sensors. Another limiting factor in the Data Sciences system is its unique, proprietary signal encoding, transmission, and receiver units. Therefore, the possibility of expanding beyond four channels (their upper limit) is quite unlikely. Coupled with the fact that these units are larger than needed and that the upper limit is 35° C. for their temperature sensors, Data Sciences units are not appropriate for this application.

Telemetry units from Mini Mitter (Sun River, Oreg.) are very small in size (XM-FH series—9.0 mm (dia.)×15 mm; VM-FH series—12 mm (dia.)×19 mm). They use the pulse interval modulation transmission mode to achieve very low power operation. However, they monitor only a single channel. Therefore, stacking several single channel transmitters to build a multi-channel device could make the combined size unacceptable. Small button-type batteries are used and are easy to replace. These units are attractive for single channel applications.

Biotelemetrics (Boca Raton, Fla.) builds transmitters whose carrier frequency is adjustable, which makes it possible to stack a series of single channel transmitters to make a multi-channel unit. The size of a typical unit is approximately 2.5 mm×7.5 mm×10 mm. The transmitters can be turned on and off periodically to reduce the power consumption. The electronics exhibits a high input impedance which enables the unit to be connected to any kind of sensor (e.g., thermistors, pH sensors, and other ion-selective sensors).

Konigsberg Instruments (Pasadena, Calif.) offers four- and eight-channel implants for measuring temperature and biopotential signals (such as EEG, ECG, and EMG) with a bandwidth up to 1 kHz. The units range in size from the smallest 1.0 cm×1.5 cm×3.3 cm to the largest 5.1 cm×2.3 cm×1.5 cm. The units are battery powered and the battery life ranges from five to 20 months. An RF switch is included to turn the battery on and off. The transmit range is typically 3–5 m. Multichannel amplifier units are also available to receive the transmissions from the implants and relay them to a remote base station. Several other small companies make biotelemetry devices (Bio-Sentry, CME Telemetrix, Coulbourn, MIE Medical, Micro Probe, Telefactor, and Transkinetics), but they are not implantable or are single-channel units (Biotelemetry Page, 1997).

Button battery cells have been available for nearly three decades, and were extensively used in hearing-aid devices. The most commonly used cells of this type are available in two chemistries—zinc-mercury oxide and zinc-silver oxide. The primary functional differences between the two are as follows: (1) zinc-mercury oxide exhibits a flatter discharge voltage characteristic over time, (2) zinc-mercury oxide responds better to momentary high-power demands (low internal resistance), (3) zinc-silver oxide has a higher output voltage, specifically 1.5 to 1.6 V, versus 1.35 V from zinc-mercury oxide, and (4) the volumetric energy density of zinc-silver (monovalent) is greater ranging 400–550 Wh/cm$^3$. The service capacity of these cells is typically near 100 mA-hours.

Another alternative to these cell types are the recent lithium-anode based cells. These cells are desirable because their output voltages (near the 3 volts needed for ICs) are typically twice that of zinc-anode cells. Another notable difference is that lithium cells are typically available in flat packages and are appropriately termed "coin-cells." From a volumetric standpoint, the energy densities of most lithium-based cells compare favorably to zinc-based cells. For example, lithium-iodine cells exhibit a 2.8 V output with a high energy density of approximately 1,000 Wh/cm$^3$. Pacemakers have used lithium cells since the 1970s.

Preferred Tumor Monitoring Devices

Figure 5:
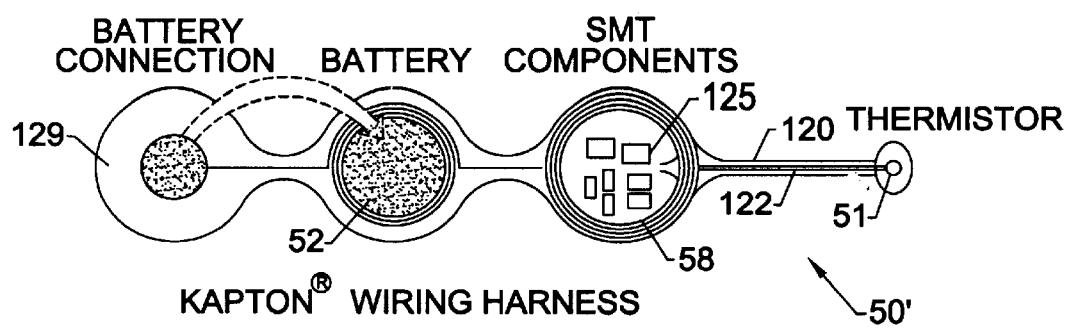
FIG. 5 is a top view of an implantable biocompatible sensor according to the present invention.
Figure 6A:
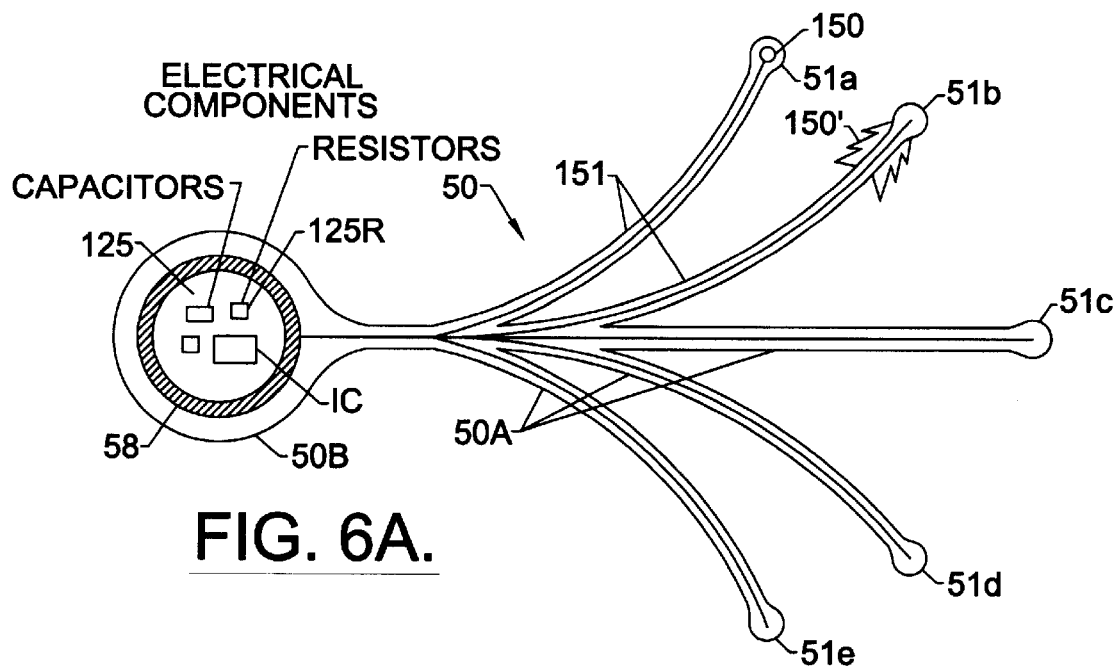
FIG. 6A is a top view of an alternative implantable biocompatible sensor according to the present invention.

Some preferred sensor embodiments of the present invention are illustrated at FIGS. 5, 6A, 8, 9, and 22. Generally described, the in situ sensor units 50 of the present invention are configured to be one of implantable or injectable into the subject. FIGS. 5, 6, 21, and 22 illustrate preferred implantable embodiments, while FIG. 8 illustrates an injectable embodiment. FIG. 9 illustrates a hybrid sensor unit 50" having both an implantable satellite sensor body 50S and associated injectable dependent sensor bodies 50D. Each of the sensor units of the present invention are powered either by a battery (FIG. 5), or, and more preferably, is inductively powered (FIGS. 6A, 8, and 9). Each of the (implantable or injectable) sensor unit bodies is hermetically sealed with biocompatible materials and sterilized by methods well known to those of skill in the art.

As shown in FIG. 5, the sensor unit 50' is configured with at least one sensor element 51. The sensor element 51 shown in FIG. 5 is a thermistor. More preferably, as shown in FIG. 6a, the sensor unit 50 comprises a plurality of sensor elements 51a–51e, which are preferably configured to monitor one or more of temperature, radiation, oxygen, and pH. Suitable discrete pH, radiation, and temperature elements 51a–51e are known to those of skill in the art. The preferred temperature sensor type is a thermistor. The preferred radiation sensors are well known such as MOSFET (metal oxide semiconductor field effect transistor) based designs. Preferred self-calibrating oxygen and combination oxygen/pH sensor embodiments will be discussed further below.

Figure 6B:
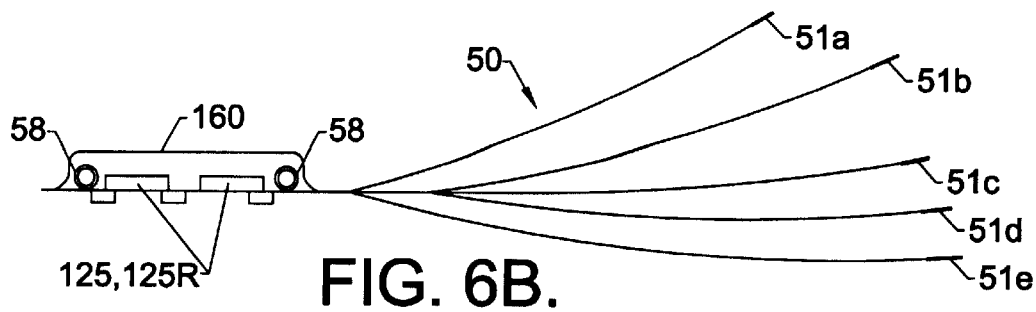
FIG. 6B is a side view of the sensor shown in FIG. 6A.

The temperature sensor element for the present invention is configured to operate in the temperature range of about 35° C. to 45° C. with an accuracy of about 0.1° C. Size is of major importance since the entire implantable device should be minimally invasive. Preferably, the entire implantable sensor unit is sized to be less than about 1.0 cm$^3$. Further, the sensor units 50, 50', 50" of the tumor monitoring system 10 are configured to operate even when exposed to a radiation field. That is, the sensor unit 50, 50', 50" do not necessarily have to function while the radiation is being administered to the tumor, but they preferably function immediately afterward. The sensor unit 50, 50', 50" is thus configured to respond quickly (within a few seconds) after radiation administration. In a preferred embodiment, as shown in FIG. 8, the sensor unit 50" is sized and configured such that it can be placed on the tip of an insertion probe and injected via a large bore canula such as via image guide placement into position. Referring now to FIGS. 6A and 6B, a preferred embodiment of a sensor unit 50 is shown. The sensor unit 50 is configured with a primary body portion 50B and a plurality of arm portions 50A extending outwardly therefrom. As shown in FIG. 6B, the arms 50A have a thin planar profile. Preferably, the arms 50A are formed of a flexible biocompatible substrate material such as a polyimide (like Kapton®, a polyimide material). At least one sensor element 51 is positioned on each arm 50A, preferably at a distal portion (away from the primary body 50B). A separate channel 151 electrically connects the sensor element 51 to the electronic operating circuitry 125 positioned on the primary body 50B. Of course, a plurality of sensor elements 51 can be positioned on each arm, each with a separate electrical communication channel 151. Preferably, each channel is defined by a pair of leads (the sensor O$_2$ may have greater than two (2) leads) formed by metal vapor deposition onto the top surface of the flexible substrate.

As is also illustrated by FIGS. 6A and 6B, the transmitter coil 58 is substantially circumferentially layered to surround the electronics 125. The electronic circuitry 125 includes at least one, and preferably a plurality, of fixed resistors 125R for signal data reference as will be discussed further below.

As shown in FIG. 6B, a biocompatible coating 160 is applied (to preferably encasulate, and more preferably, hermetically seal) to the exterior of the sensor unit 50. Surface mounted electrical components can also be located on the bottom surface of primary body 50B, with interconnection being made by plated through vias (a common method used in flexible printed circuit board technology). Advantageously, this multi-arm configuration can provide increased regional data to allow for more informal analysis of the tumor. As discussed above, the multiple sensor elements 51 can contact different locations within (penetrate at different depths) and/or wrap to contact different exterior perimeter locations along the tumor. Alternatively, one or more arms can be attached to normal tissue to provide information regarding the status of same. In any event, the sensor arms 50A are preferably configured with attachment means 150 to secure their position in the subject. For example, sensor element 51A illustrates an aperture 150 formed in a distal position of the substrate to allow a suture to attach it in position. Alternatively, sensor element 51b illustrates a barbed outer surface 150'.

FIGS. 7, 8A, and 8B illustrate a sensor unit 50" which is cylindrically shaped and sized for injection, e.g., an injectable sensor unit 50I. In this embodiment, a PCB or IC chip 125p is oriented to extend a small distance along a length of the sensor body. The coil 58 also cylindrically extends to surround a portion of the PCB or IC 125. In the embodiment shown, the PCB is a substrate (preferably a flexible substrate) which extends a distance outside the coil 58 (for an overall length which is less than about 0.5 inches). Of course, with the use of an IC configuration, this size can be further reduced. In addition, the IC or PCB can be configured and sized to extend substantially the same distance as the coil 58. The sensor body can be configured to hold a single channel (i.e., one sensor element for a PCB version having a width of about 3 mm) or multi-channel (multiple elements, with each channel layed side by side, and typically wider than the single channel version). The tip 125T of the sensor unit 50I can be configured with a rounded or pointed edge to help facilitate entry into the tumor tissue. Again, the entire sensor body is encapsulated with a biocompatible material and sterilized for medical applications.

Preferably, both the injectable and implantable versions 50I, 50, respectively, of the sensor units of the present invention, such as those shown in FIGS. 6 and 7, are inductively powered. That is, the monitoring system is configured to act as a transformer (with one coil on the surface of the patient's body and the second within the monitor) to couple and power the internally disposed sensors, as is well known to those of skill in the art and discussed briefly above. As such, the in situ sensor units 50, 50', 50", 50''' are self-contained, and have a sufficiently long service life in the body to provide clinically useful chronic information for episodic or chronic treatment decisions, and can be miniaturized without requiring catheters or externally connected wire leads into the sensors and out of the body.

Alternatively to the separate copper wire wrapped coil conventionally used to form the coil 58, the coil 58 can be integrated into the circuit board itself via a ferrite substrate (a flux concentrator). Further, the circuit board 125p and its associated electrical components can be configured as a miniaturized chip which allows the coil 58 to be similarly miniaturized. Note, however, that the signal is typically proportional to the area of the coil and, as the area of the device decreases, the signal strength associated with the coil 58 on or around the device can decrease.

It will be appreciated that to further miniaturize the device, the temperature sensor resonant element can be configured as a positive temperature coefficient (PTC) (typically ceramic). Although most conventional devices employ NTC (negative temperature coefficient) versions, for the instant application, the PTC may be advantageous.

FIG. 9 illustrates a hybrid sensor unit 50''' version of the inductively powered implantable and injectable sensor units 50, 50I described above which allows for miniaturized sensor element bodies and useful signal strength at transmission. As shown this sensor unit 50''' embodiment includes a satellite sensor unit 50S with the IC or externally communicating electronics 125 thereon and a plurality of dependent sensor units 50D. The dependent sensor units 50D are inductively coupled to the satellite sensor unit 50S which is, in turn, inductively powered and coupled to the external system. Further, the dependent sensor units 50D are telemetrically connected 60I to the satellite sensor units 50I, which is telemetrically connected 60 to the external receiver 75. Because the dependent sensor units 50D are locally positioned relative to the satellite sensor unit 50S, the signal strength demands are reduced, thereby allowing the injectable sized dependent sensor units 50D to be further reduced in size. Preferably, each dependent sensor units 50D, can be electronically encoded or identified or positionally related to a particular channel or port within the satellite sensor unit 50S to maintain relative (if not absolute) positional information for consistent data analysis of the transmitted sensor data for the monitoring system 10.

FIG. 19A illustrates another embodiment of the present invention, at least one wherein the tumor monitoring system 10''' employs a plurality of sensor units 50. That is, at least one sensor unit 50 is positioned at a different (separate) tumor site as shown. This multi-sensor unit tumor system 10''' can result in more regional specific information to adjust treatment as necessary to effective in each tumor site of concern. Preferably, the multi-sensor monitoring system 10''' will configure each separate sensor unit 50, 50", 50''' to be electronically identifiable to maintain data integrity and correlation to the tumor site/particular location. This can be provided by configuring the receiver 75 and the separate sensor units 50 (50I and 50S/50D) with port communication protocols to identify and/or maintain the relative order of transmittal to the location or position of the particular sensor unit 50 within the body (i.e., channel one for "sensor 1," channel 2 for "sensor 2," each alphanumeric identifier being manually or programmably set at insertion or position onto the tumor in relation to its left to right or up to down position to a relational axis). As the receiver 75 should be positioned proximate to the sensor unit coil 58 (typically about 30 cm) for proper data transmission, it is preferred that the receiver 75 be configured to move to overlay the appropriate sensor unit during transmission (indicated by the arrow and dotted line movement of the receiver in FIG. 19A) and it is also preferred that the receiver 75 be programmed to recognize the order of sensor unit transmission to assure data integrity. Of course, two receivers can be used, one for each sensor unit location. This may be especially appropriate for non-clinical use, such as at a patient's home wherein a patient interactive system may be needed. Thus, a dual receiver configuration, whereby a user can keep in position a portable receiver over each monitored tumor site, can be advantageous.

Of course, an external mark or indices of alignment to allow proper alignment may also be helpful (both in a single tumor/region sensor unit embodiment and a multi-sensor unit/spaced position embodiment). This can be a semi-permanent physical mark 175 made on the skin and/or other infrared or photogrammetric position readable or indication means which can cooperate with the receiver 75 (receiver loop) such that the receiver 75 can send out a position verification beam to facilitate proper alignment before/during transmission at the selected location.

For remote transmissions, the tumor monitoring systems of the instant invention are preferably configured to transmit information at a low or very low bandwidth. That is, the carrier bandwidth is preferably in the MHz range while the modulation frequency is more preferably at or below about 1 kHz. This low bandwidth operation allows transmission of signal data received from the sensors across slow communication links such as modem and voice telephone connections. Preferably, the measured signal information is encoded into one of several time-based modulation schemes. The time-based encoding permits accurate data transmission across communication links that may convey amplitude information inaccurately and frequency information accurately, such as the voice telephone network. In addition, for home site non-clinical use tumor monitoring systems 10', the monitoring equipment is preferably small and relatively inexpensive or cost-effective to be set-up and operated at remote locations.

Of course, the low bandwidth operation is not required as the data from the sensor units 50, 50I, 50S can be converted into essentially any number of suitable encoding or transmission schemes that are suitable for remote operations, as discussed above, such as substantially continuous or semi-continuous monitoring with a PC at the remote location and storing the data associated with same with time/date stamps so that a complete data set or data segment/record covering a period of hours, days, weeks, or longer can be gathered and transmitted to the central processing site over one or more discrete relatively short data transmitting sessions.

Of all of the major types of temperature sensors, typically the thermistor is by far the most sensitive. It has a fast response time and a high output for interfacing, and small devices are commercially available. The non-linear response is not critical over the small temperature range in which the sensor will function (typically less than about 10°). Although the interfacing circuits require a current source, the silicon overhead is only a few additional transistors. The device is considered fragile for industrial purposes, but should be amply rugged for this application. Sensor self-heating is reduced since the device operates in a limited temperature range and the current can be small and need not be applied continuously. If a battery source is used, the sensor element is preferably insulated or positioned spatially away to reduce its exposure to heat attributed to the battery.

To validate a tumor sensor design, a single-channel, discrete-component, commercial telemetry unit was purchased (Mini Mitter, Inc., Model VM-FH) with externally mounted thermistor. An experiment was conducted at Triangle Radiation Oncology Services (TROS) by placing the thermistor and transmitter into an agar-gel phantom target, and heating the target in a hyperthermia treatment device (Thermotron RF-8) over the therapeutic range of 37° C. to 45° C. FIG. 2A illustrates the principle of operation of a hyperperthermia treatment with a Thermotron® device. An eight MHz RF signal is applied between the plates of the machine which causes ions between them to oscillate. These oscillations generate heat by friction, producing uniform self-heating of body tissue. The agar-gel phantom is approximately the size of a human torso and mimics the heating characteristics of body tissue. During treatment sessions with a patient, the skin surface temperature is always monitored. In addition, catheters are normally inserted through the skin surface into the tumor undergoing treatment and its vicinity. During treatment, thermocouple probes are inserted through these catheters to record tumor temperatures as the RF energy is applied. These catheters are left in place in the patient between treatment sessions and are frequently a source of discomfort and infection.

This experiment was designed for two purposes. First, the performance of the insulated thermistor was compared to that of a Thermotron® thermocouple, and secondly, to observe the heating effects of the Thermotron® device's RF energy on a bare, button-sized battery placed in the agar-gel.

Figure 11:
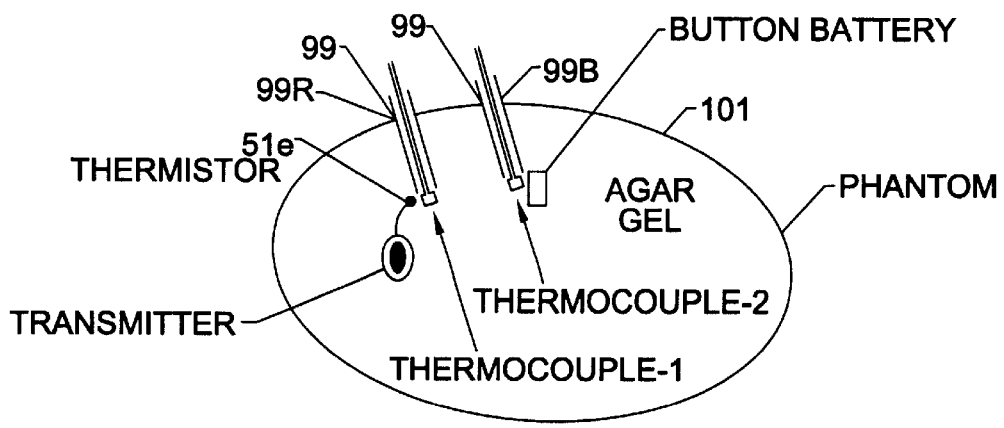
FIG. 11 is a schematic illustration of an experimental setup used to evaluate an implant tumor sensor according to the present invention.

The experimental setup is illustrated in FIG. 11. Two catheters 99 were inserted into the agar-gel phantom 101: one positioned near the thermistor 99R and the second near the battery 99B. Thermotron® device thermocouple probes were inserted into the catheters and RF energy was applied to the agar-phantom to gradually sweep its temperature over the therapeutic range. The experiment was designed to be conducted over a 75-minute time period to ensure that the agar gel was heated uniformly.

The results of the experiment are presented in Table 1. The first two columns of Table 1 show the time progression of the experiment and the temperature reading from the Thermotron® device's instrument panel taken from thermocouple-1 (see FIG. 11). This measurement was assumed to be correct and was used as the reference or "gold" standard. The third column shows the relative change in the temperature of thermocouple-1 from its initial value in the first row. The fourth row shows the relative change in the thermistor's readings at the same measurement times. Note the close correlation with the Thermotron® device's thermocouple readings.

The results of the button battery heating experiment are reported in the fifth column of Table 1. These data were recorded from a thermocouple-2 located near a button-sized battery placed in the agar-gel phantom. Note that the temperature near the battery increased to a larger extent as the RF energy of the Thermotron® device heated the agar-gel over the therapeutic range. While the temperature of thermocouple-1 near the thermistor increased by 8.8° C., the temperature of thermocouple-2 near the battery increased by 11.1° C. This indicates that any implant that is powered by a battery should be properly thermally insulated to minimize its temperature sensors that are monitoring the environment of tumor cell populations.

TABLE 1

Agar-Gel Phantom Experimental Results.

| Time (minutes) | Thermocouple-1 Temperature (° C.) | Thermo-couple-1 (T) | Thermistor (T) | Thermo-couple-2 (T) |
|---|---|---|---|---|
| 0 | 35.7 | 0 | 0 | 0 |
| 7 | 36.9 | 1.2 | 1.2 | 1.6 |
| 24 | 38.5 | 2.8 | 2.8 | 3.7 |
| 37 | 41.0 | 5.3 | 5.3 | 6.6 |
| 57 | 43.5 | 7.8 | 7.9 | 9.7 |
| 72 | 44.5 | 8.8 | 8.7 | 11.1 |

Figure 12:
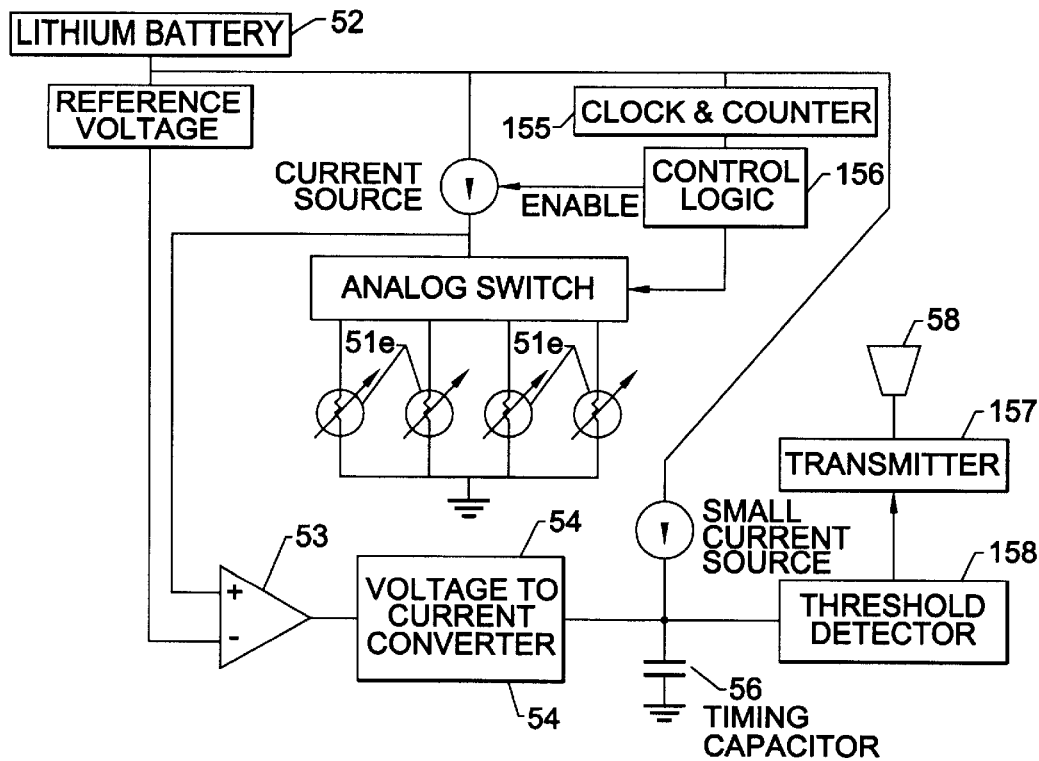
FIG. 12 is a block diagram of a circuit for an implantable sensor according to the present invention.
Figure 13:
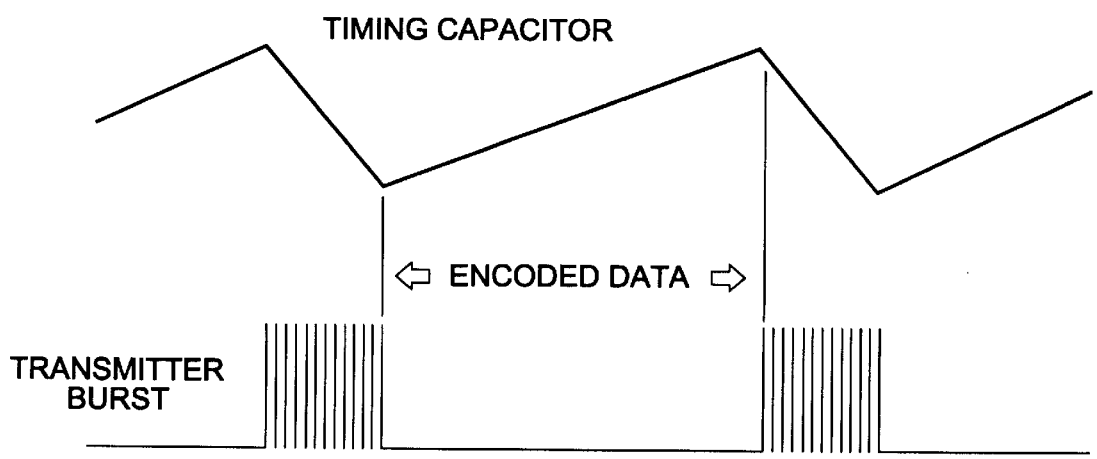
FIG. 13 is a graph of the operation of an exemplary transmitter according to the present invention.

The next task was devoted to designing and building a 4-channel, discrete-component prototype circuit using breadboarding techniques. This circuit utilized four thermistors for temperature monitoring. A block diagram of the circuit is illustrated in FIG. 12. Temperature increases were sensed by the four thermistors $51a$–$51d$ in response to a corresponding reduction in resistance. A constant current source driving the thermistors $51a$–$51d$ was used to measure the resistance. The amplifier 53 voltage output was proportional to the resistance change. A voltage to current converter 54 attached to the amplifier 53 was used to charge a timing capacitor 56. The time period for the voltage on the timing capacitor to reach a threshold was proportional to the change in resistance in the thermistor $51e$, and hence proportional to the temperature change at the thermistor's surface. FIGS. 13 and 14A–14C show suitable operational design for sensor circuits. When the capacitor voltage reaches a preset threshold, the transmitter 157 sends a signal burst at 1.0 MHz to the coil 58. At the same time, the threshold detection circuit 158 discharges the capacitor 56. At the end of the signal burst, the capacitor 56 is allowed to again begin charging toward the threshold value. If the amplifier 53 voltage is high, a large current is dumped into the capacitor 56 leading to a short charging time interval. If the voltage on the amplifier output is zero, then no current is dumped into the timing capacitor 56. In this case, a small current source was included to ensure that the device is operating properly. This small current source forced the transmitter 157 to send out signal bursts at a large time interval for testing purposes. Longer time intervals indicate lower temperature measurements, while shorter ones indicate higher temperatures.

The clock, counter, and control logic 155, 156 serve to multiplex the four thermistors $51a$–$d$ over the biotelemetry channel in a round-robin fashion. A modified AM radio receiver attached to a laptop PC running LabVIEW® software (National Instruments, Inc., Austin, Tex.) was used to detect the transmitter bursts. Water bath experiments were used to validate the operation of the implant design. The range of the telemetry link was about 30 cm.

Following the design and construction of the discrete-component breadboard, a surface-mount (SMT) unit was designed and constructed to reduce the size. The circuit of FIG. 12 was refined and a double-sided, 2.5×3.5 inch, printed-circuit (PCB) was fabricated. Low profile SMT components were used. The power consumed was 4.5 W from a 3.0 V battery. The transmitting coil 58 (13.5 mm in diameter) was formed with 25 turns of #38 AWG copper wire, producing a range of 30 cm. Four thermistors $51a$–$d$ were attached to the device and the water bath experiments were repeated. Results were similar to the earlier experiments verifying the functionality of the system.

Figure 15:
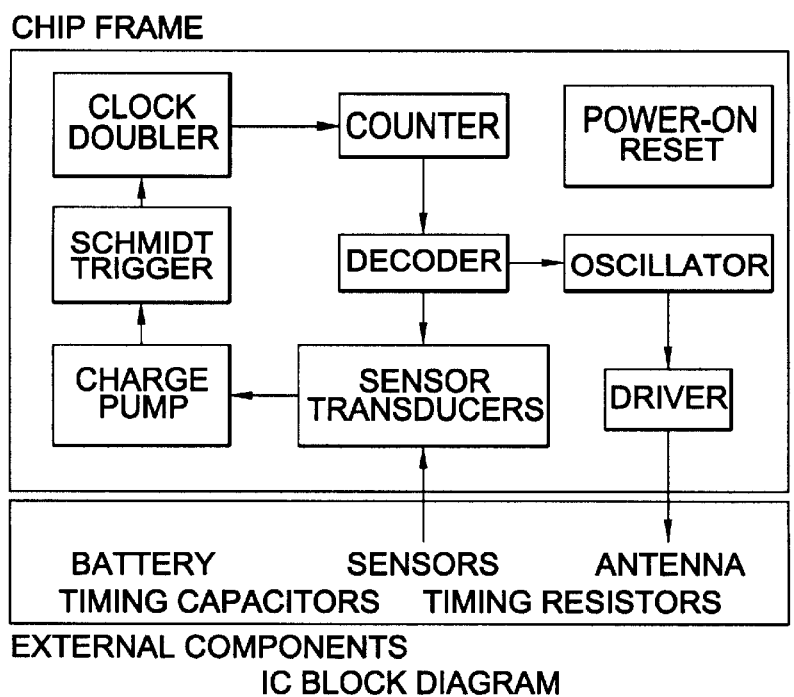
FIG. 15 illustrates an IC block diagram according to one embodiment of the present invention.
Figure 16:
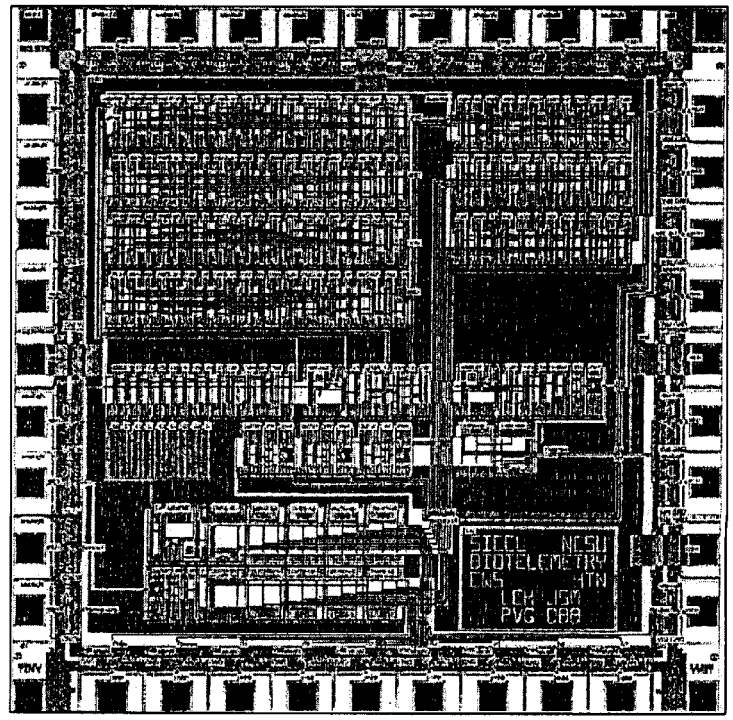
FIG. 16 is a pictorial representation of an IC layout corresponding to FIG. 15.

Following the successful SMT experiments, a first-generation integrated circuit (IC) test chip was designed. Its purpose was to demonstrate that the operating concepts adopted for the SMT unit can be adapted for integrated-circuit technology. FIGS. 15 and 16 depict the functional blocks of the IC design and its chip layout. The circuit design was first refined and simulated using SPICE. Then an IC layout was performed using standard cell technology. The circuit was specifically designed to minimize its susceptibility to latch-up. The test chip was implemented using the MOSIS fabrication service (2.0 micron, CMOS, n-well, low-noise, Orbit analog process, tiny-chip frame). Several internal test points were inserted to allow complete testing of the IC subcircuits. Four ICs delivered in dual-in-line (DIP) packages were mounted in an IC prototype unit constructed using a small PCB (1.5×4.0 cm). All four ICs were subjected to benchtop functional testing and performed as expected.

Figure 17B:
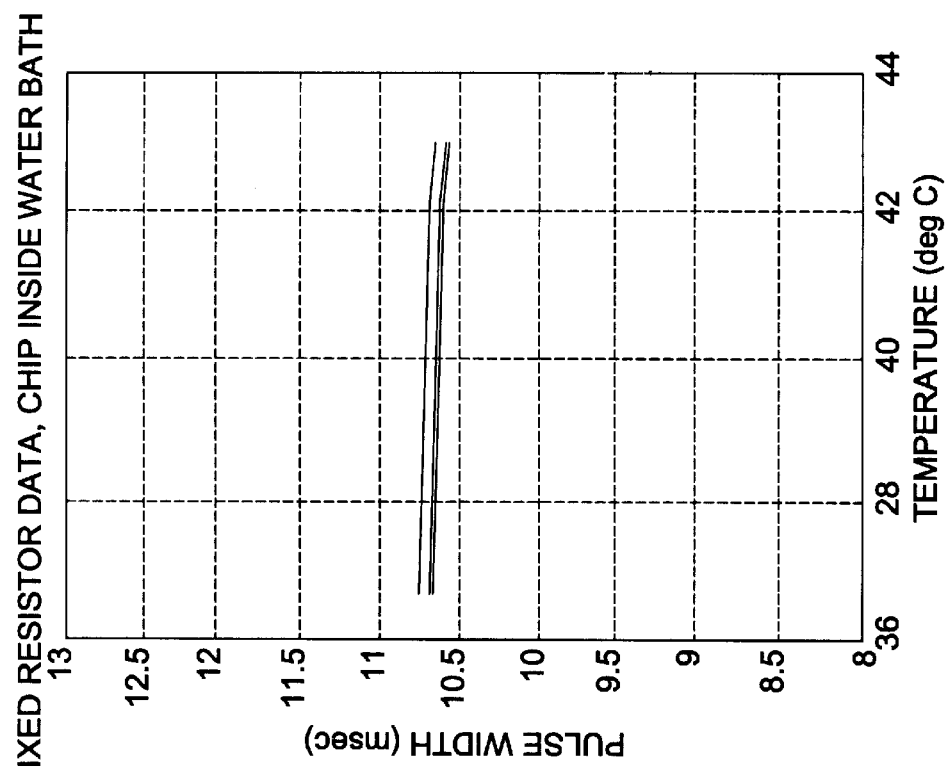
FIGS. 17A and 17B are graphs of the results of IC prototype temperature experiments.
Figure 17A:
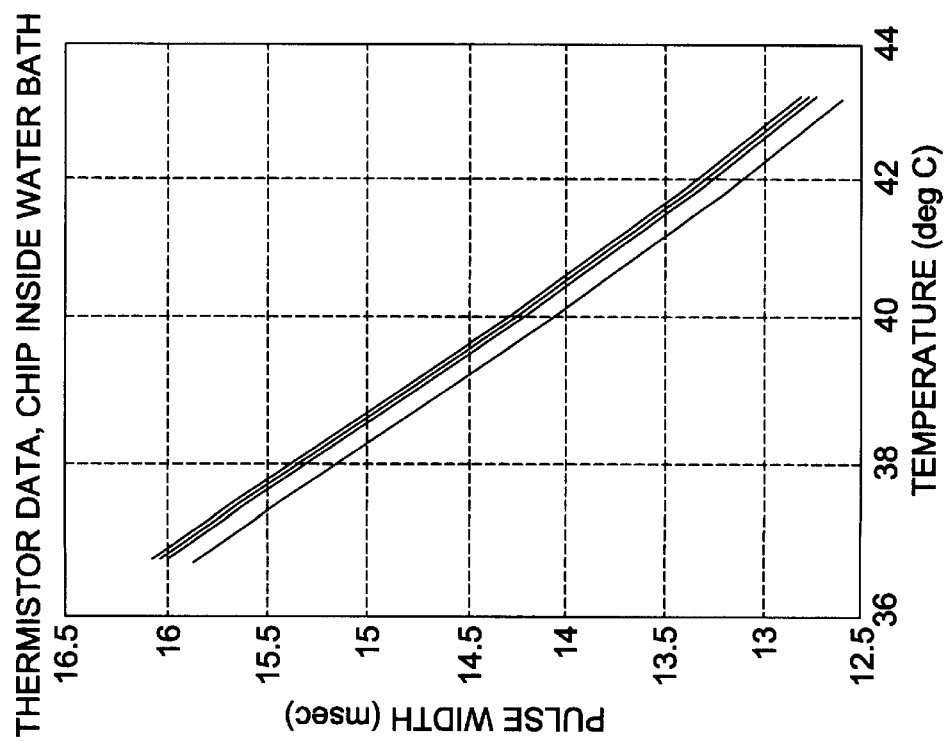

After passing the functional tests, the test chips were exposed to a series of radiation and thermal tests. First the units were thermally tested using a temperature-controlled water bath as shown in FIGS. 17A and 17B. The IC prototype unit used seven channels for sensor data. Four of the channels were connected to thermistors and the remaining three were connected to fixed resistors. FIG. 17A illustrates that the thermistors caused the channel pulse width to vary by approximately 0.03 ms per 0.1° C. while, as shown in FIG. 17B, the fixed resistor channels varied by about 0.003 ms per 0.1° C. These results are well within the accuracy specifications for tumor sensors according to the present invention.

Next the units were exposed to radiation using the cancer treatment facilities of Triangle Radiation Oncology Services (TROS) located at Rex Hospital in Raleigh, N.C. A series of 400 cGy radiation doses were delivered with a Varian Clinac 4/80 at a source to surface distance of 80 cm and a dose rate of 1.2 Gy/min. The IC prototypes were not powered during exposure, simulating one clinical environment in which the implants can be employed. The results of the radiation exposure tests are displayed in FIGS. 18A and 18B. Note that the thermistor and fixed resistor channel pulse widths change by approximately 0.001 5 ms per Gy, which translates to approximately 0.005° C. per Gy. Given that a patient is not typically exposed to more than 8000 cGy, the impact of radiation is less than 0.4° C., which can be corrected by signal processing as described below.

Figure 18B:
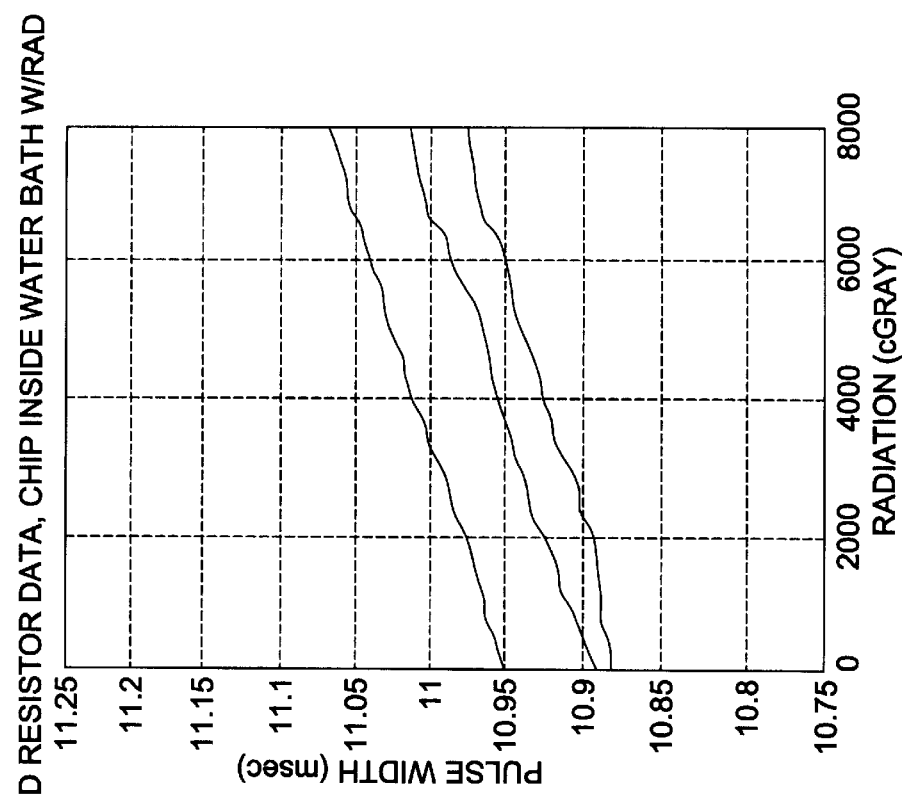
FIGS. 18A and 18B are graphs of the results of IC prototype radiation experiments.
Figure 18A:
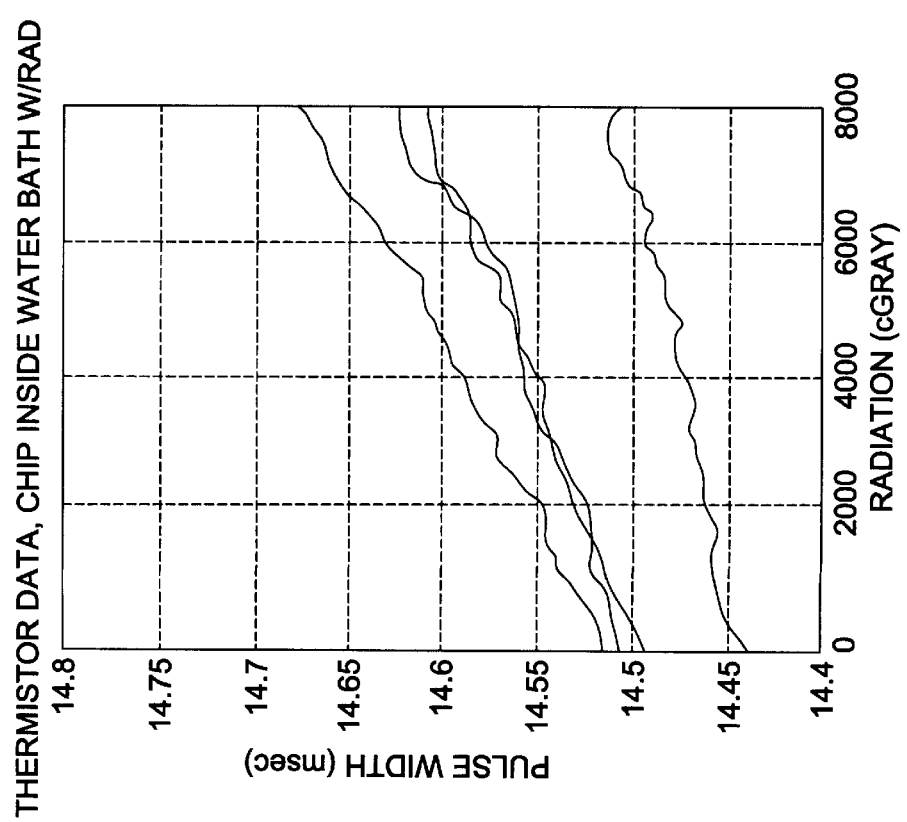

The thermistor and fixed resistor data in FIGS. 18A and 18B suggest that the increase in pulse width during exposure to radiation is due to changes in the active transistor parameters of the IC. These parameter changes are expected based on the experience of many researchers in the effects of radiation upon microelectronic circuits (NPS, 1997). Therefore, the IC device can be considered as a sensor for the radiation exposure.

Accordingly, a fixed resistor channel can be used to measure total exposure. From calibration data for each implant during manufacture, the initial pulse width for the fixed resistor channel will be known. From statistical data obtained about the behavior of the ICs under radiation exposure (data similar to FIGS. 17A and 17B), the slope of the curve will be known. Therefore, real-time measurements from the fixed resistor channel can be compensated to account for the variation based on the reference fixed resistor and known calibration data to give an accurate indication of the radiation exposure history for the implant. Using this total exposure computation, the temperature reading from the thermistor channels can be corrected mathematically to give accurate temperature reading at any radiation exposure level. That is, radiation damage or exposure can cause IC drift, and temperature drift. This is compared to three parameters: a known fixed resistor value which is constant, a temperature sensor value which varies only in response to temperature, and the IC which is affected by both (thermal and radiation). Use of the calibration data established at setup (or in the factory) can calibrate the signal data based on the number of known parameters to determine the radiation based drift and adjust for same. This drift is correctable as the dose of radiation is well within the drift adjustment as indicated by the FIGS. 17 and 18. In operation, a computer means can computationally perform the correction based on the data it receives from one or more fixed resistors.

Figure 14A:
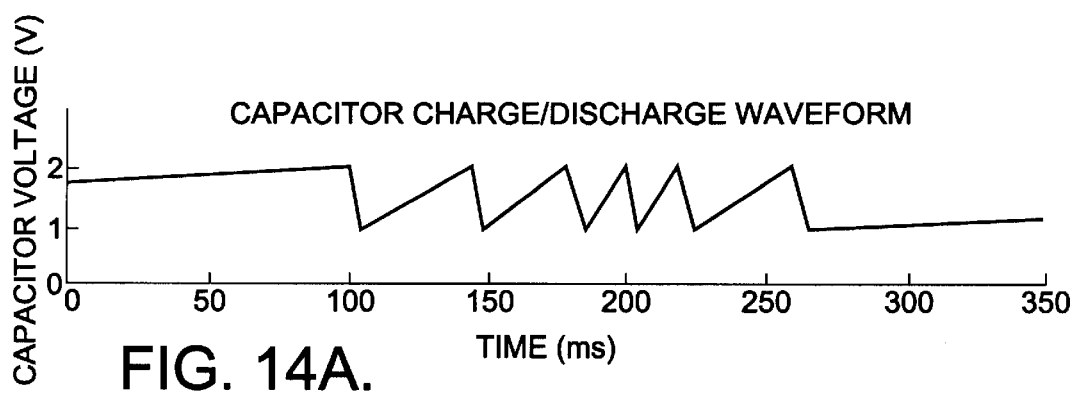
FIGS. 14A–C are graphs illustrating transmitter operational parameters according to one embodiment of the present invention.
Figure 14B:
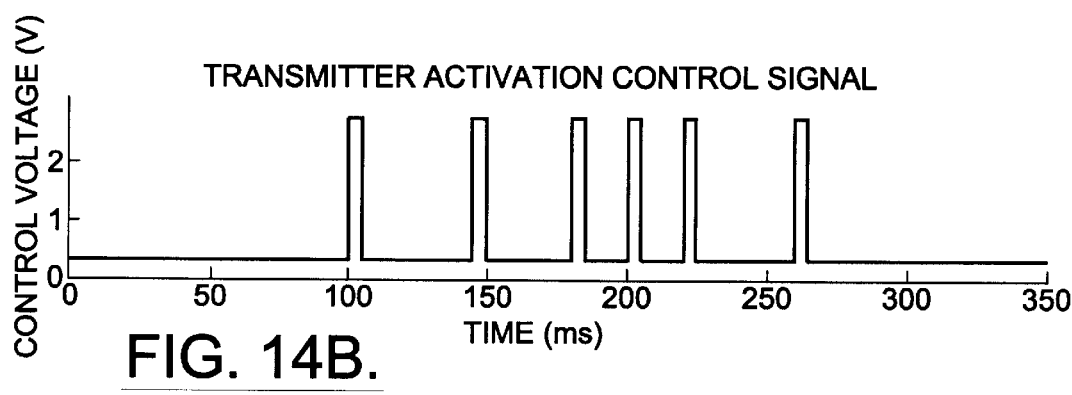
Figure 14C:
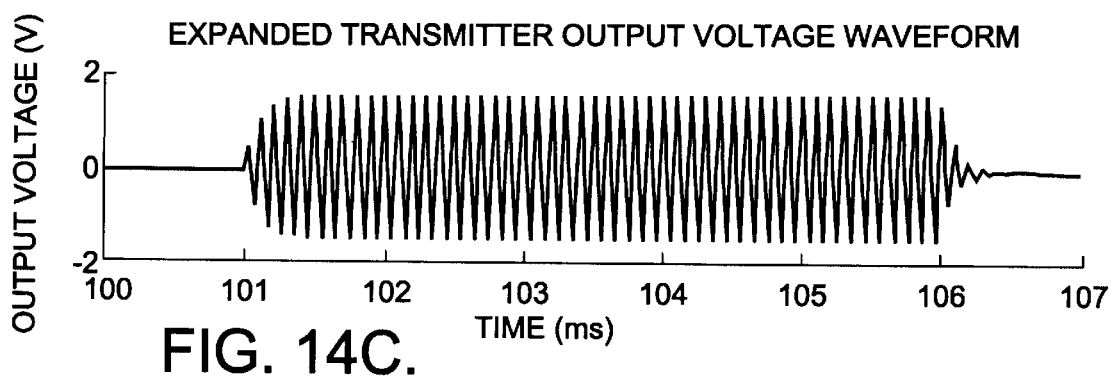

Accordingly, it is preferred that at least one fixed resistor 125R be used in the operating circuitry of the sensor, and preferably a plurality of fixed resistors. FIG. 14B illustrates one fixed resistor channel (one reference) and four active monitoring channels. In one embodiment, the sensor unit 50 includes three resistors, one is substantially invariant with temperature or radiation (the fixed resistor 125R), one changes with temperature (a thermistor), and one changes with both temperature and radiation (typically the MOSFET's in the chip have a resistance that changes with both). The thermistor has an associated measured temperature dependent curve. The fixed resistor can be used to correct the bias on the MOSFET'S (adjust or compensate for their drift due to radiation exposure/damage). The computer can give a corrected reading such as a temperature profile.

During normal operating conditions, the implant device may be powered down when radiation (high dose-rate gamma, thermal RF and microwave, or ultrasound) is applied to the patient. A series of tests were conducted to determine the effects of exposure/energy challenge events from exemplary treatment sources at Triangle Radiation Oncology Services (TROS). First, 8 MHz energy (Thermotron RF-8) at levels well above those used in treating patients was applied to the device in both its powered-down and powered-up states. Next, the tests were repeated for gamma radiation using a Varian Clinac 4/80. Finally, the tests were again repeated using microwave (915 MHz) energy from a Clini Therm surface tumor heating instrument. In all cases, the device was not damaged by the energy challenge tests, and continued to make accurate temperature measurements after the conclusion of the tests. All test were conducted on the same implant device so that the cumulative effect of the challenge tests were negative.

In order to assess biosurvivability and biocompatibility, several mock implant devices were fabricated using materials that are similar to the preferred embodiments of the sensor units described above. The overall scheme for fabricating a mock implant is highlighted in FIG. 5. The substrate 120 can be fabricated using five-mil flexible Kapton® polyimide material covered by a 25 micron copper layer. The metal layer 122 is patterned using photolithography into the wiring harness for a simple oscillator circuit. Next, an insulating layer of polyimide can be deposited and patterned to open conducting vias to the metal traces. Then surface mount electrical components 125 are placed and soldered to the substrate. Next, a thermistor 51 is connected to the end branch of the implant substrate as shown in FIG. 5. Then a coil of antenna wire 58 is mounted with the IC and/or SMT components 125 as illustrated in the figure. Finally, a lithium coin-shaped battery 52 is attached to the substrate 120. The battery 52 is first affixed to the substrate in the position shown in FIG. 5. The end flap 129 (the circle that contains the second battery connection) is then folded over the battery and attached using conducting silver epoxy. The entire device is then encapsulated in a biocompatible material such as a thin layer of silastic and/or medical-grade silicone to protect it from the biological environment during implant.

Additional features can also be included in sensor units 50, 50', 50", 50''' based upon the specification of the user interface. For example, the ability to turn the battery on and off with an externally applied RF signal can be included in an IC (chip) design. Another feature can be the inclusion of pH sensor interface electronics. The pH sensors will preferably be implemented on a biocompatible, flexible substrate such as the Kapton® substrate shown in FIG. 10A (Cosofret, 1995). This design is compatible with the Kapton® substrate shown in FIG. 5.

Figure 20:
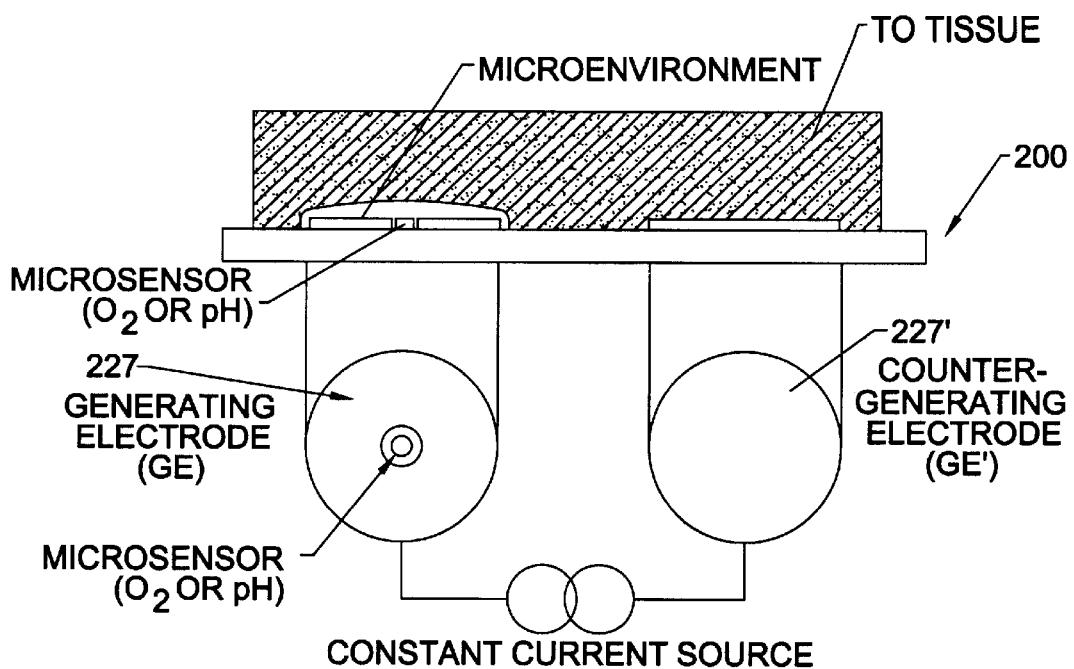
FIG. 20 is a schematic illustration of a self-calibrating in situ, in vivo microsensor.
Figure 22:
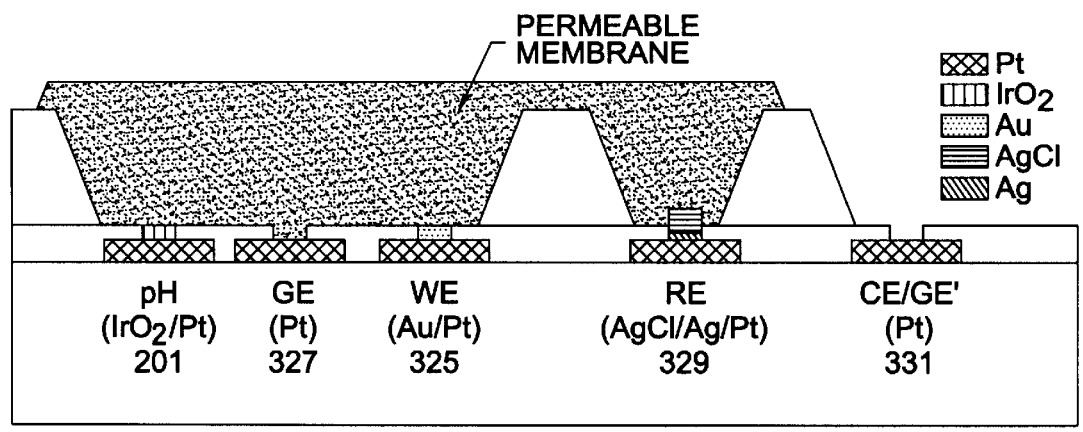
FIG. 22 is a section view of a self-calibrating combination pH and $O_2$ sensor.

In one preferred embodiment, the present invention employs selfcalibrating oxygen, pH, or combination oxygen/pH sensors. The operating principle of the in situ, in vivo self-calibrating chronically implanted sensor units 200, 201, 300 is based on water electrolysis at noble metal electrodes as shown in FIGS. 20 and 22. Oxygen or hydrogen can be evolved by the electrolysis of water by applying a current through a generating electrode ("GE") 227 and counter-generating electrode ("GE'") 227' for a certain period. Accumulation of these dissolved gas molecules at the GE 227, in turn, rapidly establishes a microenvironment of oxygen saturation or hydrogen saturation in close proximity to the microsensor. A two-point calibration procedure for the oxygen sensor unit 200 can then be performed, with the high point calibration being established in an oxygen-saturated phase, and the low point calibration in an oxygen-depleted phase that is produced by saturating the microenvironment with hydrogen. These transient perturbations of the microenvironment are expected to equilibrate rapidly with the surrounding medium (tissue). With this in situ, in vivo self-calibration sensor units 200, 201, 300 periodic sensor calibration can be performed to check the operability and biosurvivability of a chronically implanted device.

It is preferred that the self-calibrating sensor units 200, 201, 300 be configured with the following operational and physical specifications:

(1) Dynamic range:
   (a) 0–760 mm Hg with at least 10 mm Hg resolution (for oxygen tension) and/or
   (b) pH 5.0–8.0 with pH resolution of about 0.1;
(2) Concurrent operation during hyperthermia treatment sessions; and
(3) Minimum 4–6 week (preferably 6 week or 1.5 month) period of operation and more preferably at least a 3 month period of operation.

The water electrolysis method can be extended to perform a one point, in situ, in vivo calibration of an implanted pH sensor unit 201 (FIG. 10B) as well. A micro pH sensor unit 201 that is surrounded by a generating electrode will experience a titrating pH microenvironment during water electrolysis. If one repeatedly drives the electrolysis current forward and backward through the generating electrode, the highest slope in the time response of the pH sensor will occur at the moment of neutral pH (pH 7.0). Thus, a one-point calibration at neutral pH can be performed during water electrolysis by checking the first derivative of sensor response during titration. The functionality of similar pH titrating microdevices has been demonstrated for a pH-static enzyme sensor or buffer capacity sensor (Olthuis, 1992). This prior work strongly supports the feasibility of one point pH calibration as an option in tumor monitoring applications.

Previously, polarographic micro-oxygen sensors were fabricated on flexible Kapton® material. The basic electrochemical three-electrode cell configuration shown in FIG. 21 was adopted to avoid current flow and minimize surface material consumption in a micro-reference electrode. All electrodes were designed to be geometrically symmetric to assure diffusional mass transport of electrochemical species in all radial directions.

Two different designs were considered—one with rectangular bands and another with concentric circles. The design with concentric circles gave better performance, which can be explained theoretically. The noise at an electrode-electrolyte interface is generated by two sources (Lambrechts, 1992)—white noise and 1/f noise. A lower form factor for the electrode (the circumference to surface area ratio) results in a lower white noise level, which implies that the noise generated by circular electrode is lower than that by a band electrode with the same geometric area. The 1/f noise is inversely proportional to the electrode area. Also, magnitude of current output is proportional to the electrode area. This means that current output level and 1/f noise limits the scaling of amperometric sensors to extreme small size for tissue oxygen measurements.

Figure 21:
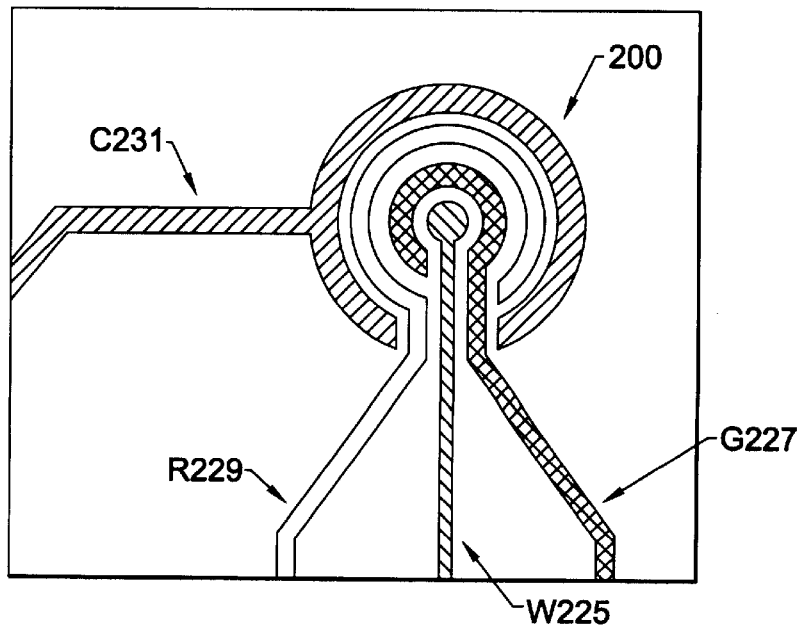
FIG. 21 is a photograph of a self-calibrating oxygen sensor.

The layout for both configurations were performed using 20, 10, and 5 micron line widths. FIG. 21 is a photograph of the fabricated prototype oxygen sensor 200 (concentric configuration). All noble metal electrodes were made of gold, the material that has been shown to possess the best stability when used as an oxygen catalyzer (Hoare, 1984).

Figure 10A:
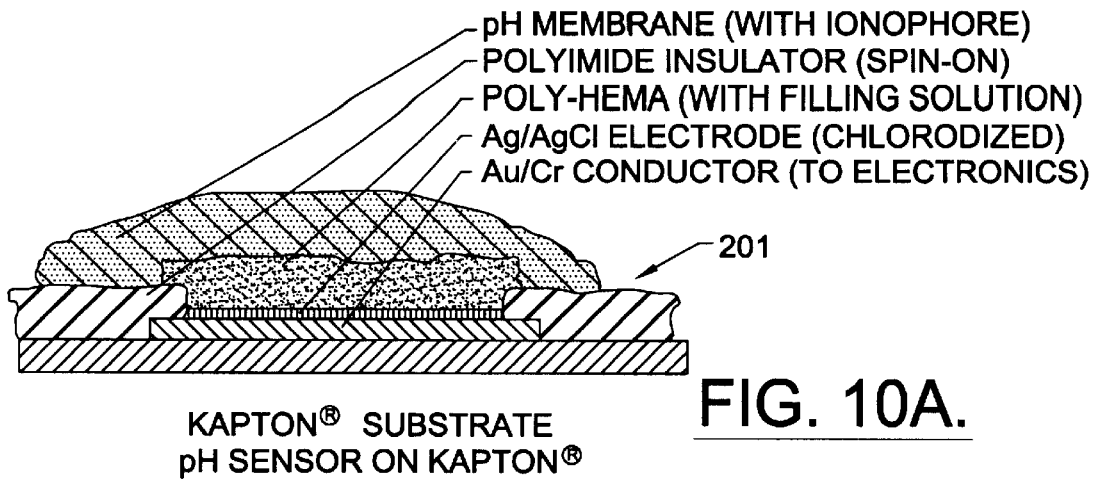
FIG. 10A is a greatly enlarged cutaway front view of a mock implant of a pH sensor with a pH (ionophore) membrane according to the present invention.
Figure 10B:
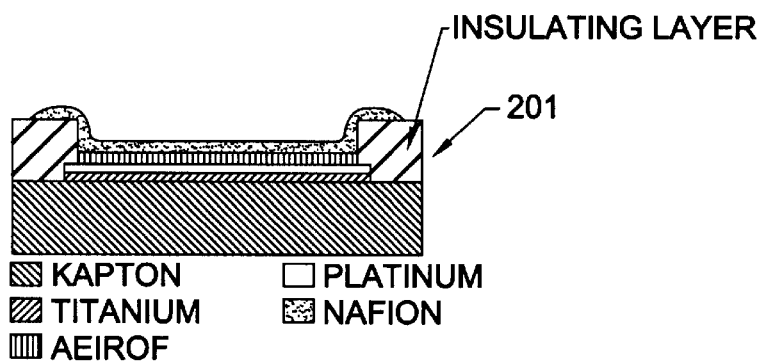
FIG. 10B is a side view of an alternate embodiment of a pH sensor (with iridium oxide).

Turning now to the function of each concentric circle shown in FIG. 21, the middle electrode serves as a working electrode ("WE") 225 at which dissolved oxygen molecules are electrochemically reduced. The GE 227 is wrapped around the working electrode; this configuration will establish oxygen-saturated or hydrogensaturated microenvironments during self-calibration cycles. Proceeding from inside to outside, the next concentric circle is used as the reference electrode ("RE") 229. The outermost electrode in FIG. 21 is the counter electrode ("CE") 231 of this three-electrode cell. It is placed as far as possible from the WE 225 to eliminate electrochemical interference at the WE of byproducts generated at the CE 231. The GE' 227' (not shown) is also located remotely from the WE 225 for this same reason. the past, pH sensors have also been fabricated on flexible substrates (Cosfret, 1995). FIG. 10A illustrates a pH sensor structure containing a p-HEMA central dome over a Ag/AgCl electrode. The final fabrication step is the deposition of the outer polymeric membrane containing the pH ionophore. These sensors have performed accurately in preliminary tests in vivo in blood for up to two. months. The size of these potentiometric sensors are preferably minimized to improve their capability for resolving spatial gradients. Further size reduction of the pH sensors shown in FIG. 10A may be limited by the manual deposition of the polymeric membrane solution, weaker adhesion to the substrate and high impedance, as the membrane contact area is diminished. Another drawback imposed by the use of polymeric membranes is the potential for leakage and degradation of membrane's plasticizer and ionophore for long-term operation. More recently, work has been done to miniaturize pH sensors by replacing the polymeric membrane by a solid state analogue. The best alternative identified to date is iridium oxide which has been shown to possess excellent pH-sensing capability and can be deposited on the sensor surface using a simple electroplating method (Marzouk, 1998). This new structure is shown in FIG. 10B.

Self-calibrating $O_2$ sensors, such as shown in FIG. 21, have been fabricated by facilities in BMMSL (Biomedical Microsensors laboratory) at North Carolina State University. Tables 2 and 3 summarize a preferred fabrication process of oxygen sensors 200 and pH sensors 201, respectively.

TABLE 2

Oxygen Sensor Process

| Process Steps | Process Details |
| --- | --- |
| Substrate selection | 3-mil Kapton ® VN |
| Cleaning | Organic solvent cleaning and dehydration |
| Metal Deposition | DC Magnetron sputtering 200 Å Cr followed by 2000 Å Au |
| Photolithography | Spin coated 1.3 $\mu$m Shipley 1813 photoresist,. Contact exposure with Tamarack Alignment and Exposure System. (Exposure energy optimized for 5-$\mu$m linewidth.) |
| Metal Etching | Wet chemical etching |
| Cleaning | Organic solvent cleaning and dehydration |
| Polyimide process | Spin coated 2-$\mu$m Pyralin PI-2721 photosensitive polyimide. Contact exposure with Tamarack system. Spin development and thermal curing in atmosphere |

TABLE 3 pH Sensor Process

| Process Steps | Process Details |
| --- | --- |
| Substrate selection | 5-mil Kapton ® VN |
| Cleaning | Organic solvent cleaning and dehydration |
| Metal Deposition | DC Magnetron sputtenng 200 Å Ti followed by 2000 Å Pt with shadowmask |
| Cleaning | Organic solvent clean and dehydration |
| P2Y | |

TABLE 3-continued pH Sensor Process

| Process Steps | Process Details |
| --- | --- |
| olyimide process | Spin coated 5-$\mu$m Pyralin PI-2721 photosensitive polyimide. Contact exposure with Tamarack system. Spin development and thermal curing in atmosphere |
| Electrodeposition | Electroplate IrO$_x$ according to the established method (Marzouk, 1998) |

Another preferred embodiment of an in situ sensor unit is shown in FIG. 22 as a combination pH/O$_2$ sensor unit 300. As the combination sensor unit 300 assumes smaller feature sizes, the area of the generating electrode and, thus, its current carrying capacity, is reduced. A smaller structure will also enable the new sensors to be employed in linear arrays for gradient measurements. The microenvironment of the smaller sensor may require less oxygen to become saturated. Once the GE 327 has established a saturated microenvironment, these conditions will be dissipated rapidly unless structural measures are taken to delay oxygen and pH equilibration. Hence, the self-calibrating design can employ a recessed structure (a micropool) to sustain the saturated microenvironment for a limited sensor calibration period. Thus, a 3-dimensional micropool can be configured by using layers of photosensitive polymers to build walls to confine the working and generating electrodes 325, 327. The volume of the micropool can also determine the overall sensor unit 300 performance and the time period needed for calibration. A near optimum design can be determined by iterating several of the design parameters in various fabrication runs. It is noted that some surface degradation and adhesion problems at the polyimide/metal interface at the electrode edges were observed during prototype experiments (at current densities exceeding 10 mA/cm$^2$).

The conventional Clark oxygen sensor contains a reference electrode (anode) and a working electrode (cathode) located in the same compartment encapsulated by hydrophobic, electrically non-conducting membrane. In contrast, the instant design separates the RE 329 and WE 325 to allow a space for the GE 227 (positioned therebetween and placed to control the micro environment of the WE 225) as illustrated in FIGS. 21 and 22. This new arrangement is in contrast to the conventional Clark sensor, which may not be suitable for long-term implantation due to the risk of membrane rupture and the subsequent degradation of the sensor's internal filling solution. In this design, the separated RE and WE are electrically coupled via a hydrophilic permeable membrane and tissue fluids. This separated configuration for the RE and WE can cause difficulties due to increased solution resistance when the anode is very far from the cathode. However, the 3-electrode system reduces this effect. Another difficulty can be introduced by WE surface contamination due to direct contact with components of tissue fluid that penetrate the permeable membrane. As such, it is preferred that the electrode material used be selected to reduce this behavior. For example, it has demonstrated (Holmstrom, 1998) that a bare gold electrode, implanted up to 4 years for oxygen monitoring, absorbed less blood proteins than a glassy carbon electrode, and no adverse tissue reactions were observed.

To minimize any electrostatic coupling between the 3-electrode cell and generating current source, the operation of the sensor 300 is preferably divided into separate calibration and measurement modes. To simplify the device structure, the counter electrode (CE) will preferably serve a dual as the counter-generating electrode (GE') of generating source. Thus, a single electrode that can be switched between the two operational modes and can serve both functions.

Preferably, to reduce the feature size and reliably form same during fabrication, a silicon wafer-supported flexible substrate process is used to reduce thermal expansions and surface roughness distortions. In this fabrication process, polyimide (DuPont P12723) is spin-cast to a thickness of about 25 $\mu$m onto a thermal oxide coated silicon wafer. After all sensor processing steps have been completed, the wafer is soaked in a dilute H.F. solution. The thermal oxide is etched away and thereby releasing the flexible polyimide substrate and its sensor structures.

A recessed sensor structure can also be implemented using photosensitive polymer materials. Thicknesses of up to 30 $\mu$m can be obtained with a 2-step spincoating procedure. Other materials are also available for this purpose. For example, a dry film (DuPont Pyralux or Vacrel which have thicknesses of 25 to 100 $\mu$m) can be laminated over the device using a thermal vacuum process. The highest aspect ratio (depth:width) for the micropool that can be fabricated using these laminated films is typically about 1:1. This ratio can be maintained for depths from 10 to 100 $\mu$m.

Platinum is known as the best noble metal electrode for water electrolysis and is easily deposited and patterned using microfabrication technology. In previous experiments with physiological solutions containing rich chloride ions, surface chloridation of gold generating electrodes was observed during the positive potential region of water electrolysis. This problem should be alleviated by replacing the gold generating and counter electrodes with platinum. For simplicity, in photo-processing steps, a titanium platinum layer will serve as both electrodes and wiring leads. To generate the other electrode surfaces, gold can be electroplated (for the working electrode) and silver (for the reference electrode) onto the platinum layer. For the pH sensor, iridium oxide will also be plated. The devices are designed so that the electroplating steps are self-aligning, and no additional photopatterning will be required. These procedures have already been established (Marzouk, 1998). Currently, the preferred permeable membrane material is p-HEMA covered with polystyrene or collodion (Kreuzer, 1980).

Figure 23A:
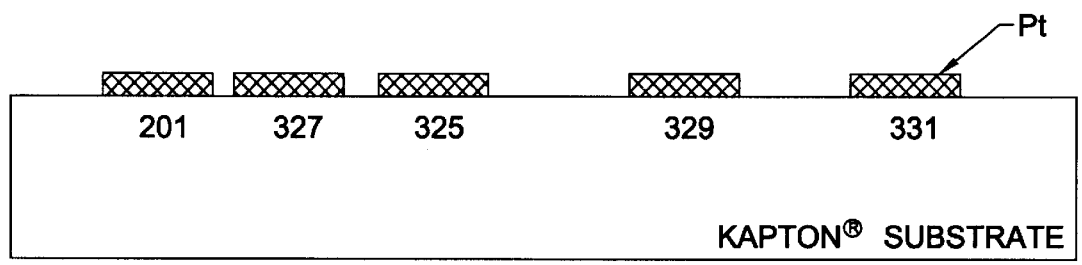
FIGS. 23A–23C are side views of the sensor of FIG. 22 illustrating a fabrication sequence.
Figure 23B:
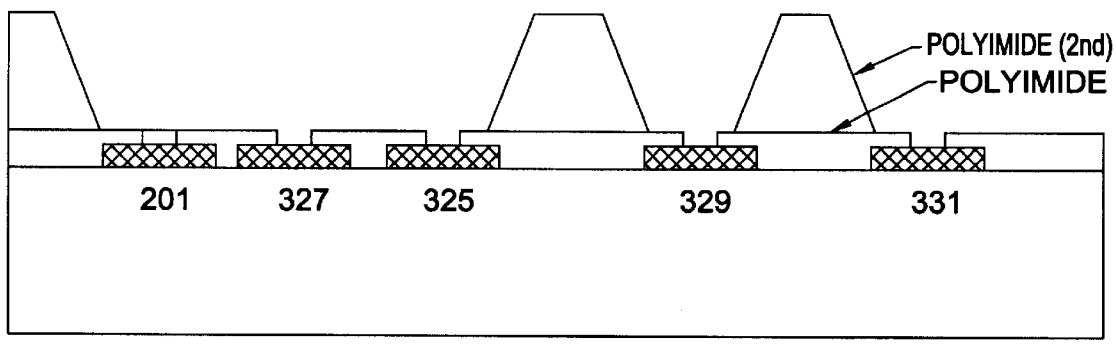
Figure 23C:
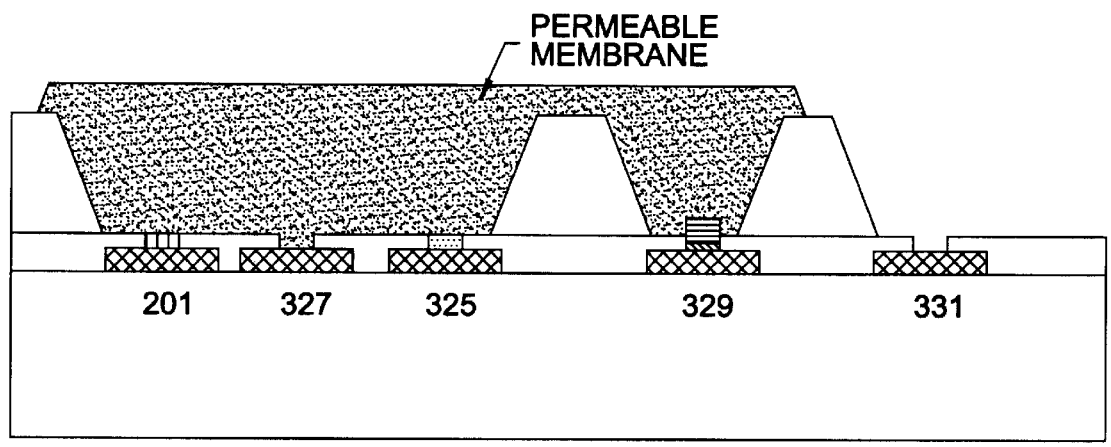

The overall process sequence is shown in FIGS. 23A–23C. Platinum is deposited by sputtering and then patterned by photolithography. Next, a thin layer of polyimide is spin-coated and patterned to define the various electrode areas and to insulate the wiring conductors. Then a thick polymer micropool is defined around working electrode and reference electrode area by a lamination process. Next, gold (as the oxygen catalyzer) or iridium oxide (as the pH-sensitive layer) will be electroplated, followed the plating and chloridation of silver (as the RE). Finally, a permeable membrane is cast by micromanipulation and cured. In operation, it should be noted that with continuous polarizing voltage during oxygen sensor operation, one disadvantage can be a relatively large oxygen consumption and power consumption as well as aging effect. This power consumption is preferably reduced to provide electrode stability. Thus, intermittent or periodic measurement are preferably instituted with a potential step. Necessary calibration parameters such as current density and duration can be determined for proper calibration of periodic measurements.

The present invention is explained further in the following examples. These examples are for illustrative purposes only, and are not to be construed as limiting of the invention.

EXAMPLE

A patient presents with an unresectable lung cancer (adenocarcinoma or squamous cell). The conventional accepted treatment is a combination of radiation and chemotherapy. The radiation is given everyday, Monday through Friday, and the chemotherapy (taxol and cisplatin) are administered either once a week in low doses or every three weeks in higher doses. All patients are treated in substantially the same manner and the expected response rate is between 50–75%. Therapy is not individualized despite the fact that it is known that oxygen levels, pH, and particularly, cell doubling times, may vary widely between patients.

The availability of the methods, systems, and implantable sensors of the present invention which are configured to monitor pH, oxygen, and radiation, now offer a more customized approach to therapy. The sensors can be positioned in situ in the tumor at different penetration depths or across different regions of the tumor to provide regional specific information. Specific values or oxygen, pH, and cell proliferation can be established either prior to initiation of treatment by a predictive statistical norm in an established data base, or during initial treatment to define relative values, the specific values are identified as either a "go" for treatment or a "no go" for treatment to determine when and if a treatment should be commenced. A monitoring algorithm can be used to quantify important values of variables and an affirmative attempt can be made to correct each variable to reach or approximate the desired specific levels at treatment. For example, to manipulate the tumor to achieve oxygenation of about 50–52 mm Hg over a substantial volume of the tumor, as well as to exhibit a lower tumor pH of about 6.8, and to stimulate or identify and deliver during periods of increased cell proliferation.

Following the initial dose of radiation or chemotherapy, each variable will be monitored to determine an appropriate time (associated with a favorable treatment period) to deliver the next dose of radiation and/or chemotherapy. Preferably, each patient is monitored at least four times each day following treatment to establish a specific response pattern for an individual patient. Utilizing this ongoing, periodic monitoring approach can allow delivery of any cytotoxic agent in a more precise and favorable manner and/or to withhold treatment during tumor treatment resistant periods. It is preferably to treat when all variables indicate that the tumor is vulnerable such as when there is an indication of high oxygenation level, low pH, and increased cell proliferation. It the variables do not synchronize to indicate a favorable index at the same time, then a statistical regression analysis can be identified to define an appropriate treatment time. It will be appreciated that in addition to radiation and chemotherapy, hyperthermia and/or other treatments can be incorporated into the treatment protocol, especially in tumors exhibiting a high hypoxic fraction. This can allow for increased cell kill, after which the kinetics of the tumor will change and allow for more precise delivery of the radiation and/or chemotherapy. Thus, the individualized treatment will allow the delivery of cytotoxic agents at a favorable treatment time to achieve increased tumor cell kill, and thereby increase the response of the tumor to the treatment. In this example, when a satisfactory response has been obtained, the tumor can be removed.

In summary, the individualization of therapy can now be instituted based on obtaining information on the dynamic changes within each individual patient's tumor. This information should lead to increase tumor cell kill, increased survival and decreased morbidity. This should translate into a decrease in the cost of treating patients by a decrease in morbidity and therefore less hospitalization; increase the effectiveness of cytotoxic agents by allowing for delivery of increased dose or even a decrease in the dose through more efficient timing of delivery of the cytotoxic. The present invention can monitor and provide information on dynamic changes occurring within a tumor.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clause are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

Literature Cited

Adam, M. F. et al., "Oxygen tension measurements of tumors growing in mice," *Int. J. Radiation Oncology Biol. Phys.,* Vol. 45, 1998, pp. 171–180.

Akin, T., Z. Babak; K. Najafi, "RF telemetry powering and control of hermetically sealed integrated sensors and actuators," Proc. Solid-State Sensors & Actuators Workshop, Hilton Head, S.C., 1990, pp. 145–148.

Akin, T., K. Najafi, R. M. Bradley, "An implantable multichannel digital neural recording system for a micromachined sieve electrode," Proc. Int. Conf. on Solid-State Sensors and Actuators, Stockholm, Sweden, June 1995, Vol. 1, pp. 51–54.

Biotelemetrics, Inc., 6520 Contempo Lane, Boca Raton, Fla. 33433, Tel: 407-394-0315.

Biotelemetry Page, http://speed.nimh.nih.gov/telemetry/classx.html, Feb. 1997.

Chaudhary, P. M., I. B. Robinson, "Expression and activity of p-glycoprotein, a multidrug efflux pump, in hematopoictic cefls," *Cell,* Vol. 66, 1992, pp. 85–94.

Cosofret, V. V., M. Erdosy, T. A. Johnson, and R. P. Buck, "Microfabricated sensor arrays sensitive to pH and K+ for ionic distribution measurements in the beating heart," *Analytical Chemistry,* Vol. 67, 1995, pp. 1647–53.

Data Sciences International, 2678 Patton Road, St. Paul, Minn. 55113–1136, Tel: 800-262-9687 or 612-636-0461, Fax: 612-636-1095.

Deutsch, S., "Fifteen-electrode time-multiplex eeg telemetry from ambulatory patients," *IEEE Transactions on Biomedical Engineering,* Vol. BME-26, 1979, pp. 153–159.

Dewhirst, M. W., "Concepts of oxygen transport at the microcirculatory level," *Seminars in Radiation Oncology,* Vol. 8, 1998, pp. 143–150.

Donald, J., R. Martin, "A microminiature hybrid multichannel implantable biotelemetry system," *Biotelemetry Patient Monitoring,* Vol. 8, 1981, pp. 163–172.

Fernald, K., T. Cook, T. Miller, III, J. Paulos, "A microprocessor-based implantable telemetry systems," *Computer,* Vol. 24, No. 7, 1991, pp. 23–30.

Fernald, K. W., "A microprocessor-based system for the fast prototyping of implantable instruments for biomedical research applications", Doctoral Dissertation, Elect. & Computer Eng., NC State Univ., 1992.

Fryer, T., H. Sndler, W. Freund, E. McCutcheon, E. Carlson, "A multichannel implantable telemetry system for flow, pressure, and ECG measurements," *Jour. of Applied Physiology*, Vol. 39, 1973, pp. 318–326.

Gilligan, B. J., R. K. Rhodes, M. C. Shultz, S. J. Updike, "Evaluation of a subcutaneous glucose sensor out to 3 months in a dog model," *Diabetes Care*, Vol. 17, 1994, pp. 882–887.

Goldie, J. H., A. J. Coldman, "The genetic origin of drug resistance in neoplasm: implication for systemic therapy," *Cancer Research*, Vol. 44, 1994, pp. 3643–3663.

Graichen, F., G. Bergmann, "Four-channel telemetry system for in vivo measurement of hip joint forces," *Journal of Biomedical Engineering*, Vol. 13., 1991, pp. 370–374.

Graichen, F., G. Bergmann, A. Rohlmann, "Inductively powered telemetry system for in vivo measurement with orthopaedic implants," Proc. Biotelemetry XIII, Williamsburg, Va., Mar. 1995, pp. 75–80.

Gray, et al. *The concentration of oxygen dissolved in tissue at the time of irradiation as a factor in radiotherapy*, Br J Radiol 26:638–648, 1953.

Gschwend, S., J. Knutti, H. Allen, J. Meindl, "A general-purpose implantable multichannel telemetry system for physiological research," *Biotelemetry Patient Monitoring*, Vol. 6, 1979, pp. 107–117.

Hansen, B., K. Aabo, J. Bojsen, "An implantable, externally powered radiotelemetric system for long-term ECG and heart-rate monitoring," *Biotelemetry Patient Monitoring*, Vol. 9., 1982, pp. 228–237.

Hines, J. W., C. J. Somps, B. Ricks, L. Kim, "Advanced biotelemetry systems for space life sciences: pH telemetry," Proc. Biotelemetry XIII, Williamsburg, Va., Mar. 1995, pp. 131–137.

Hoare, J. P., "A cyclic voltammetric study of the gold-oxygen system," *J Electrochem. Soc.*, Vol. 131, No. 8, 1984, pp. 1808–1815.

Holmstrom, N., P. Nilsson, J. Carlsten, S. Bowald, "Long-term in vivo experience of an electrochemical sensor using the potential step technique for measurement of mixed venous oxygen pressure," *Biosensors & Bioelectronics* 13, 1998, pp. 1287–1295.

Jain et al., "Determinants of tumor blood flow: A review," *Cancer Res*, Vol. 48, 1988, pp. 2641–2658, 1988.

Konigsberg Instruments, Inc., 2000 Foothill Boul., Pasadena, Calif. 91107, Tel: 818-449-0016.

Kreuzer, F., Kimmich, H., Brezina, M., Heyrovsky, J., "Polarographic determination of oxygen in biological materials," *Medical and Biological Applications of Electrochemical Devices*, 1980, pp. 173–261.

LabVIEW® Version 4.0 Reference Manual, National Instruments, Inc., Austin, Tex., 1995.

Lambrechts, M., Sansen, W., *Biosensors. Microelectrochemical Device*, NY, N.Y.: IOP Publishing Ltd., 1992, pp. 206–208.

Linden, D. Handbook of Batteries. McGraw-Hill, 1995.

Lindner, E., V. V. Cosofret, S. Ufer, T. A. Johnson, R. B. Ash, H. T. Nagle, M. R. Neuman, and R. P. Buck, "In vivo and in vitro testing of microelectronically fabricated planar sensors designed for applications in cardiology," *Fresenius Journal of Analytical Chemistry*, Vol. 346, 1993, pp. 584–588.

Loeb, G. E., C. J. Zamin, J. H. Schulman, P. R. Troyk, "Injectable microstimulator for functional electrical stimulation," *Med. & Biol. Eng. & Comput.*, Volume 29, 1991, pp. NS13-NS19.

Lowe, S., et al., "p53 status and the efficacy of cancer therapy in vivo," *Sci.*, Vol. 266, 1994, pp. 807–810.

Mackay, R. S., *Bio-Medical Telemetry*. Second edition. New York, N.Y.: IEEE Press, 1993.

Marzouk, et al., in "Electrodeposited Iridium Oxide pH electrode for measurement of extracellular myocardial acidosis during acute Ischemia," 70 Anal. Chem. No. 23, 1998, pp. 5054–5061.

Mini Mitter Inc., P.O. Box 3386, Sun River Oreg. 97707, Tel: 503-593-8639, Fax: 503-593-5604

Mueller, J. S., H. T. Nagle, "Feasibility of inductive powering of miniature low-power biotelemetry for use with microfabricated biomedical sensors," Proc. Biotelemetry XIII, Williamsburg, Va., March 1995, pp. 372–377.

Nardin, M., K. Najafi, "A multichannel neuromuscular microstimulator with bidirectional telemetry," Proc. Int. Conf. on Solid-State Sensors and Actuators, Stockholm, Sweden, June 1995, Vol. 1, pp. 59–62.

NPS, Annual Meeting of the IEEE Nuclear and Plasma Science Society, 445 Hoes Lane, Piscataway, N.J. 08855, 1997.

Olthuis, W., Bergveld, P., "Simplified design of the coulometric sensor-actuator system by the application of a time-dependent actuator current," *Sensors and Actuators B*, Vol. 7, 1992, pp. 479–483.

Oshima, H., H. Funakubo, T. Dohil, Y. Okabe, T. Katoda, T. Mitsuoka, A. Takeuchi, T. Uchida, "Development of micro-telemetering, multi-sensor capsule system with newly developed LSI for clinical applications," Proc. Int. Conf. on Solid-State Sensors and Actuators, 1987, pp. 163–166.

Puers, B., P. Wouters, M. DeCooman, "A low power multichannel sensor interface for use in digital telemetry," *Sensors and Actuators A*, Vols. 37-38, 1993, pp.260–267.

Reichert, W. M., S. S. Saavedra, "Materials considerations in the selection, performance, and adhesion of polymeric encapsulants for implantable sensors," in D. F. Williams (editor), *Medical and Dental Materials*. New York: VCH Publishers, Inc., 1992, pp. 303–343.

Robinson, S. P., F. A. Howe, L. M. Rodrigues, M. Stubbs, J. R. Griffiths, "Magnetic resonance imaging techniques for monitoring changes in tumor oxygenation in blood flow," *Seminars in Radiation Oncology*, Vol. 8, 1998, pp. 197–207.

Thermotron RF-8 Technical Manual, Thermotron Corp., Tokyo, Japan.

Sakata, K., et al., "Hypoxia-induced drug resistance: Comparison to P-glycoprotein-associated drug resistance., *Br. J. Cancer*, Vol. 64:, 1991, pp. 809–814.

Schweiki, et al., "Vascular endothelial growth factor induced by hypoxia may mediate hypoxia-initiated angiogenesis," *Nature* 359:843–854, 1992.

*Seminars in Radiation Oncology*, Vol. 8, 1998, pp. 141–142.

Stratford et al., "Manipulation and exploitation of the tumor environment for therapeutic benefit," *Int J Radiat Biol* 65:85–94, 1994.

Sutherland et al., "Tumor hypoxia and heterogeneity: Challenges and opportunities for the future," *Semin Radiat Oncol* 6; 59–70, 1994.

Ueda, K., Y. Itou, N. Kawai, K. Tozawa, K. Kohri, M. Shinkai, T. Kobayashi, "Development of targeting hyperthermia on prostatic carcinoma and the role of hyperthermia in clinical treatment," *Jpn. J. Hyperthermic Oncol.*, Vol. 15 (supplement), 1999, pp. 18–19.

Varian Clinac 4/80 Technical Manual, Varian Corp., Irvine, Calif.

Webster, J. G. (editor), "Design of Cardiac Pacemakers," New York, N.Y.: IEEE Press, 1995.

Williams, M., J. Nurmi, "Multipurpose chip for physiological measurements," *Proc.* 1994 *IEEE International Symposium on Circuits and Systems,* Vol. 4, p.255–258.

Wouters, P., M. De Cooman, R. Puers, "A multi-purpose CMOS sensor interface for low-power applications," *IEEE Journal of Solid-State Circuits,* Vol. 29, No. 8, August 1994, pp. 952–956.

Young et al., "Hypoxia induces DNA overreplication and enhances metastatic potential of murine tumor cells," *Proc Natl Acad Sci USA,* Vol. 85, 1997, pp. 9533–9537

Young, R. C., V. T. DeVita, "Cell cycle characteristics of human solid tumors in vivo," *Cell Tissue Kinetics,* Vol. 3, 1970, pp. 285–290.

That which is claimed is:

1. A method of monitoring and evaluating the status of a tumor undergoing treatment, comprising the steps of:
   (a) monitoring in vivo at least one physiological parameter associated with a tumor in a subject undergoing treatment with an in situ sensor unit;
   (b) transmitting data associated with the at least one monitored physiological parameter from the in situ positioned sensor unit to a receiver located external to the subject;
   (c) analyzing the transmitted data to determine a condition of the tumor;
   (d) repeating steps (a), (b), and (c) periodically at a plurality of sequential points in time; and
   (e) evaluating a tumor treatment strategy comprising at least one of:
       identifying a favorable or unfavorable tumor treatment time for administration of at least one of a radiation, drug, and chemical therapy;
       evaluating the efficacy of at least one of therapeutic radiation, drug, and chemical treatment on the tumor;
       determining the amount of radiation delivered in vivo to the tumor site;
       monitoring radiolabeled drug uptake at the tumor site; and
       analyzing the transmitted data to monitor the influence of at least one of a thermal, chemical, or radiation therapy on the tumor based on data transferred before, during and after the therapy.

2. A method according to claim 1, wherein the at least one monitored physiological parameter includes the temperature proximate the tumor site and at least one of the pH at the tumor site, the level of oxygenation at the tumor site, cell proliferation at the tumor site, and the amount of radiation exposure at the tumor site, and wherein said transmitting and analyzing steps are repeated sufficiently to track variation in the at least one of the monitored parameters and thereby assess the behavior of the tumor over time.

3. A method according to claim 1, wherein said monitoring step monitors a plurality of tumor physiological parameters, and wherein said analyzing step defines a plurality of predetermined test conditions, wherein at least one test condition associated with identifying a favorable treatment time and at least one test condition associated with identifying an unfavorable treatment time, and wherein said method further comprises the step of alerting a clinician as to when the transmitted data satisfies one of said test conditions which identifies when a favorable unfavorable treatment window for delivering a subsequent active treatment to the tumor is identified.

4. A method according to claim 3, wherein said favorable treatment test condition includes test criteria corresponding to the identification of a tumor susceptibility or vulnerability phase.

5. A method according to claim 2, wherein said transmitting step comprises transmitting data from a non-clinical site of a patient to a remote clinical site thereby allowing remote dynamic monitoring of the at least one physiological parameter.

6. A method according to claim 1, wherein steps (a) and (b) are repeated temporally proximate to an active treatment delivery of at least one of a radiation therapy and a chemotherapy to provide real-time information regarding the tumor and the appropriateness of proceeding with the active treatment at that time.

7. A method according to claim 1, wherein steps (a) and (b) are repeated during an active therapeutic cytotoxic chemical treatment delivery to provide real-time information to a physician to allow therapeutic treatment decisions based on the substantially real time monitored tumor parameters.

8. A method according to claim 1, wherein a therapeutic oncology treatment protocol is adjusted based on tumor information provided by the monitored in vivo physiological parameter of the tumor particular to the subject.

9. A method according to claim 1, wherein said repeating step is carried out at least once every 24 hours.

10. A method according to claim 1, wherein the repeating step is carried out at varying time intervals responsive to the progression or stage of treatment and responsive to detected relative changes in the monitored parameters.

11. A method according to claim 1, further comprising electronically storing a series of temporally related data measurements to dynamically monitor the variation in the at least one monitored physiological parameter overtime.

12. A method according to claim 1, wherein the tumor is one of carcinoma and scarcoma.

13. A method according to claim 1, wherein the tumor is a solid mass.

14. A method according to claim 1, further comprising the step of positioning at least one sensor unit configured to monitor a plurality of physiological parameters into a subject such that it is positioned in in situ in vivo contact with a target tumor, wherein the positioned sensor unit has a service life of at least about 4–10 weeks.

15. A method according to claim 1, wherein said monitoring step is performed by a sensor unit with a plurality of sensor elements positioned in situ, and wherein said sensor unit is positioned in the subject by at least one of implanting and injecting the sensor unit such that at least one of the sensor elements contacts the tumor.

16. A method according to claim 14, wherein said positioning step comprises injecting multiple discrete dependent sensor units into the subject such that they contact the target tumor and further comprises implanting a satellite sensor unit in wireless electrical communication with said dependent sensor units into the subject such that the satellite sensor is positioned proximate to said dependent sensor units.

17. A method according to claim 1, wherein said evaluating step includes at least one of determining the efficacy of the treatment and identifying a subsequent active favorable treatment window.

18. A method according to claim 17, wherein the subject has multiple tumors, and wherein said method further comprises positioning a first sensor unit in situ to contact a first tumor and positioning a second sensor unit in situ proximate to a second tumor different from the first tumor.

19. A method according to claim 15, wherein at least one of said sensor elements is configured to monitor the toxic effects of treatment on normal cell tissue proximate to the tumor.

20. A method according to claim 1, said method further comprising the step of monitoring at least one parameter associated with normal cells proximate to the tumor.

21. A method according to claim 20, wherein said normal cell monitoring parameter is pH and wherein said at least one monitored tumor parameter is pH.

22. A method according to claim 21, wherein said analyzing step compares the normal cell pH with the tumor pH and wherein said evaluating step includes reviewing the relative difference between the two pH parameters to establish a treatment strategy.

23. A method according to claim 1, wherein said monitoring step monitors a plurality of different tumor physiological parameters.

24. A method according to claim 23, wherein said plurality of different tumor physiological parameters comprises pH, oxygenation, temperature, and quantification of the amount of radiation therein.

25. A method according to claim 23, wherein said monitoring step comprises detecting a period of increased cell proliferation and an increased level of oxygenation.

26. A method according to claim 15, wherein said multiple sensors have an extended clinically useful life of about at least 4–6 weeks.

27. A method according to claim 23, wherein said monitoring step monitors at least two of temperature proximate the tumor site, oxygenation level proximate the tumor site, delivered radiation proximate the tumor site, and pH level proximate the tumor site, and wherein said analyzing step predetermined test criteria evaluates the presence of at least one of an elevated oxygenation level, an elevated radiation level, and a decreased pH level.

28. A method according to claim 1, wherein said evaluating step comprises the steps of tracking the results of the monitored data over a period of time and comparing the transmitted data against a predictive model to determine when a planned therapeutic tumor treatment indicates an adjustment is desired based on deviation of the tumor's response to the delivered therapy as measured against a population norm.

29. A method according to claim 1, wherein said predetermined test criteria includes absolute and relative test conditions.

30. A method according to claim 1, wherein said analyzing step identifies the amount of time elapsed from the time of the last active radiation or chemotherapy treatment.

31. A method according to claim 2, wherein said analyzing step tracks a dynamic history of at least two of the monitored parameters over time.

32. A method according to claim 20, further comprising administering one of a cytotoxic agent and radiation to the subject, and assessing the toxic effects on normal cell tissue proximate to the target tumor site.

33. A method according to claim 1, said method further comprising establishing a known active treatment date and known active treatment dose, wherein said monitoring step monitors the amount of treatment dose received at the tumor, and wherein said analyzing step compares the received dose with the known dose and identifies a discrepancy from the delivered dose to the measured dose to thereby confirm the efficacy of a targeted treatment dose.

34. A method according to claim 15, wherein said sensor unit includes sensor electronics, and wherein said method further comprises the step of adjusting the transmitted data to account for deviations in the data attributed to the sensor unit's exposure to at least one of radiation and temperature.

35. A method according to claim 3, wherein the predetermined test criteria identifies the presence of a clustering of test conditions including the presence of an elevated oxygenation level and a period of cell proliferation measured corresponding to an elevated radiation level at the tumor.

36. A method according to claim 1, wherein said evaluating step includes adjusting a chemical or radiation treatment dose, delaying or advancing the next active treatment delivery of one of a chemical, radiation, and thermal therapy, or altering a selected treatment therapy type of one of chemical, radiation, or thermal to a different one.

37. A method according to claim 3, wherein said method further comprises automatically scheduling an active treatment session or evaluation appointment at a clinic.

38. A method according to claim 1, wherein said monitoring step is carried out remotely over at least one of a telephone line, fiber optic line, cable line, a computer modem, an internet hook-up, and other wireless communication mode.

39. A method according to claim 1, wherein said monitoring step is carried out via at least one sensor unit having a plurality of in situ sensor elements having a service life of at least about 4–10 weeks, and wherein said method further comprises the step of locally transmitting data associated with the at least one monitored physiological parameter representative of a physiological condition associated with the tumor thereby providing substantially real-time information regarding the condition of the tumor.

40. A method according to claim 39, wherein said local transmitting step is performed before an active therapy session to determine the suitability of delivering an active treatment.

41. A method according to claim 39, wherein said local transmitting step is performed during an active radiation, chemical, or thermal therapy session to control at least one of the amount, rate, or length of an active treatment session.

42. A tumor monitoring system for identifying enhanced active cancer treatment windows, comprising:

at least one implantable sensor unit comprising a plurality of sensor elements and associated sensor electronics, wherein a plurality of said plurality of sensor elements are configured for in vivo in situ contact with a cancerous tumor in a subject undergoing treatment for cancer, and wherein said sensor elements are configured to detect a plurality of different parameters associated with the tumor and wirelessly transmit data associated with the detected parameters, wherein said plurality of different parameters includes at least two of the amount of radiation exposure at the tumor site, extracellular pH of the tumor, pH of normal tissue, tumor cell oxygenation, tumor cell proliferation and temperature;

a remote receiver in wireless communication with said at least one sensor, said receiver configured to receive the transmitted data, wherein said receiver is spatially separate from said at least one sensor and positioned external to the subject; and a processor having computer readable program code for analyzing the transmitted data to identify the presence or absence of a favorable cancer treatment condition.

43. A tumor monitoring system according to claim 42, further comprising computer readable program code means for reviewing and adjusting the received transmitted data to correct for variations in the signal data attributed to environmental exposure of the sensor unit or sensors elements held in the subject.

44. A tumor monitoring system according to claim 42, wherein, in position, said plurality of sensor elements are configured to reside at different locations on and within the tumor, and wherein at least one of said plurality of sensor elements is configured to contact normal tissue cells proximate to the tumor.

45. A tumor monitoring system according to claim 42, wherein said remote unit is configured to be worn by the subject, and wherein said remote receiver further comprises a remote interface to allow a user to transmit data from a physically remote non-clinical site to a central processing unit at a clinical site during a non-emission cancer treatment period.

46. A tumor monitoring system according to claim 42, wherein said sensor unit is configured as a cylindrically shaped body having opposing first and second ends, and wherein said sensor unit includes an inductively coupled power source, wherein said sensor is sized to have a length which is less than about 0.5 inches (1.27 cm) and is configured to be injectable via a trochar into the subject such that at least one of said first and second ends contacts a tumor within a mammalian body, and wherein said at least one sensor unit has an implanted service life of at least about 4–10 weeks.

47. A tumor monitoring system according to claim 42, wherein said sensor unit comprises operating electronics positioned within a first body portion and a plurality of flexible arms extending outwardly therefrom, each of said arms having distal portions containing at least one sensor element thereon and having at least one signal path between said operating electronics in said first body portion to each of said sensor elements in each of said arms.

48. A tumor monitoring system according to claim 42, wherein said sensor unit includes an inductively coupled power source, and wherein at least one of said arms includes a plurality of sensor elements.

49. A tumor monitoring system according to claim 42, wherein said arms are configured with an anchor portion to positionally attach to a desired portion of the tumor.

50. A tumor monitoring system according to claim 42, wherein said sensor elements include at least one pH sensor element, at least one oxygen sensor element, at least one temperature sensor element, and at least one radiation sensor element.

51. A tumor monitoring system according to claim 42, wherein said at least one sensor unit comprises a plurality of sensor elements is configured as an implantable satellite sensor unit and an associated plurality of injectable discrete dependent sensor units, wherein each of said discrete dependent sensor units have at least one sensor element thereon, and wherein said plurality of discrete dependent sensor units are in wireless communication with said satellite sensor unit.

52. A tumor monitoring system according to claim 42, wherein said at least one sensor unit is a plurality of sensor units, and wherein each sensor unit includes a unique identifier to allow transmitted data to be correlated to the appropriate in situ sensor unit position.

53. A tumor monitoring system according to claim 42, wherein said remote receiver is portable and wearable by the patient so as to be held proximate thereto.

54. A computer program product for monitoring and analyzing the condition of a tumor in a patient undergoing cancer treatment, the computer program product comprising:

a computer readable storage medium having computer readable program code means embodied in said medium, said computer-readable program code means comprising:

computer readable program code means for commencing a first wireless data transmission from an in situ wireless sensor with at least one sensor element positioned in a subject proximate to a tumor site undergoing treatment for cancer, the data transmission including data corresponding to the output of the at least one sensor element;

computer readable program code means for commencing a second wireless data transmission from the in situ sensor temporally separate from the first wireless data transmission;

computer readable program code means for tracking variation between the first and second data transmissions to provide a dynamic behavioral model of the tumor's response to the treatment;

computer readable program code for analyzing the transmitted data to identify at least one favorable cancer treatment opportunity;

computer readable program code means for evaluating at least one of (a) the amount of radiation exposure delivered to the tumor site from a cancer radiation treatment session, (b) cell proliferation associated with the tumor, (c) the response of normal tissue proximate the tumor site to the cancer treatment; (d) the value of at least one physiological or biological parameter of the tumor to evaluate efficacy of a cytotoxic or targeted drug or chemical treatment or to confirm delivery of the cytotoxic or targeted drug or chemical treatment to the tumor site, (e) a variation in the value of a physiological or biological parameter of the tumor from a predictive model, (f) the presence of an unfavorable cancer treatment period, and (g) the value of at least one physiological or biological parameter of the tumor to identify a receptiveness for a particular cancer therapy type.

55. A computer program product according to claim 54, wherein said computer readable program code means for evaluating includes computer program code means for evaluating the efficacy of the cancer treatment by comparing the value of at least one predetermined physiological or biological parameter to a corresponding predetermined value established for each of the at least one physiological or biological parameters.

56. A computer program product according to claim 54, wherein said computer readable program code means for evaluating includes computer program code means for evaluating the efficacy of the cancer treatment by comparing the value of at least one predetermined physiological or biological parameter to a corresponding relative change in the monitored at least one physiological or biological parameters, over time.

57. A computer program product according to claim 54, further comprising computer readable program code means for commencing ongoing periodic data transmissions over a predetermined time period, the predetermined time period including time away from a clinical treatment site, and computer readable program code means for analyzing the periodic data transmissions to identify a favorable active cancer treatment opportunity.

58. A computer program product according to claim 54, further comprising computer readable program code means for initiating a subsequent data transmission temporally proximate to a planned treatment time to thereby provide real time information for therapeutic decisions regarding the condition of the tumor in a manner which can estimate the likelihood of success of a planned treatment strategy.

59. A computer program product according to claim 58, further comprising computer readable program code means for initiating a subsequent data transmission during an active treatment session to thereby provide real time information for therapeutic decisions regarding the treatment session itself.

60. A computer program product according to claim 59, further comprising a computer readable program code means for controlling the delivery of the treatment itself corresponding to a change in the one or more monitored physiological parameters during the treatment session.

61. A computer program product according to claim 54, further comprising computer readable program code means for remotely directing the transmission of data from a non-clinical site to a clinical or data processing site remote from the non-clinical site for offsite evaluation.

62. A computer program product according to claim 57, wherein said ongoing periodic data transmissions monitors the at least one physiological parameter at least at sequential semi-continuous time intervals, and wherein said computer program product comprises computer readable program code means for storing the semi-continuously monitored data transmissions and then subsequently transmitting the stored data transmissions as a bulk update to a clinical site.

63. A computer program product according to claim 54, wherein said computer program code means evaluates a plurality of said items (a) through (e).

64. A computer program product according to claim 63, wherein said computer program code means evaluates at least three of said items (a) through (e).

65. A computer program product according to claim 64, wherein said computer program code means evaluates all of said items (a) through (e).

66. A computer program product according to claim 63, wherein said computer readable program code means for evaluating the value of at least one physiological or biological parameter of the tumor to evaluate efficacy of a cytotoxic or drug or chemical treatment or to confirm delivery of the cytotoxic or drug or chemical treatment to the tumor site comprises comparing the pH of the subject's normal tissue to the extracellular pH of the tumor tissue.

67. A computer program product according to claim 63, wherein said computer readable program code means for evaluating the value of at least one physiological or biological parameter of the tumor to evaluate efficacy of a Cytotoxic or drug or chemical treatment or to confirm delivery of the cytotoxic or drug or chemical treatment to the tumor site comprises comparing the extracellular pH of the subject's cancerous tumor tissue to a predetermined value before delivery of an active cancer treatment.

68. A computer program product according to claim 63, wherein said computer readable program code means for evaluating the amount of radiation exposure delivered to the tumor site during a cancer radiation treatment session confirms that the radiation level received at the tumor site is between about 3000–6000 cG.

69. A computer program product according to claim 63, wherein said computer readable program code means for evaluating a variation in the value of a physiological or biological parameter of the tumor from a predictive model compares the physiological or biological values of the tumor to a statistical model of values at corresponding periods of time into comparative treatment regiments.

70. A computer program product according to claim 63, wherein said computer readable program code means for evaluating the value of at least one physiological or biological parameter of the tumor identifies an unfavorable cancer treatment period associated with when the tumor is hypoxic.

71. A computer program product according to claim 63, wherein said computer readable program code means for evaluating the value of at least one physiological or biological parameter of the tumor identifies a favorable cancer treatment period associated with when the tumor is in an active cell proliferation phase.

72. A computer program product according to claim 63, wherein said computer readable program code means for evaluating the value of at least one physiological or biological parameter of the tumor to identify a receptiveness for a particular cancer therapy type identifies the extracellular pH level of the tumor for assessing which drug to administer to the patient.

* * * * *

UNITED STATES PATENT AND TRADEMARK OFFICE
Certificate

Patent No. 6,402,689 B1                                Patented: June 11, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Charles W. Scarantino, Raleigh, NC (US); H. Troy Nagle, Durham, NC (US); Leslie C. Hall, Raleigh, NC (US); Jeffrey Mueller, Cary, NC (US); and Bahram Ghaffarzadeh Kermani, San Diego, CA (US).

Signed and Sealed this Fifteenth Day of September 2009.

HENRY M. JOHNSON, III
*Supervisory Patent Examiner*
Art Unit 3769